(12) United States Patent
Zhu et al.

(10) Patent No.: US 8,280,483 B2
(45) Date of Patent: Oct. 2, 2012

(54) MULTI-MODALITY MEDICAL IMAGE VIEWING

(75) Inventors: Yang-Ming Zhu, Solon, OH (US); Xiangyu Wu, Hudson, OH (US); Charles A. Nortmann, Richmond Heights, OH (US); Ronald W. Sukalac, Mentor, OH (US); Steven M. Cochoff, Chagrin Falls, OH (US); L. Alan Love, Chesterland, OH (US); Richard Cheng-Hsiu Chen, Hudson, OH (US); Chris A. Dauterman, Aurora, OH (US); Madhavi Ahuja, Shaker Heights, OH (US); Dawn M. Maniawski, Chagrin Falls, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1876 days.

(21) Appl. No.: 11/424,147

(22) Filed: Jun. 14, 2006

(65) Prior Publication Data

US 2008/0008401 A1    Jan. 10, 2008

(51) Int. Cl.
*A61B 5/05* (2006.01)
(52) U.S. Cl. ........ 600/407; 600/410; 600/436; 600/437; 382/294; 345/1.1
(58) Field of Classification Search .................. None
See application file for complete search history.

(56) References Cited

U.S. PATENT DOCUMENTS

| | | | |
|---|---|---|---|
| 5,672,877 A | 9/1997 | Liebig et al. | |
| 5,740,267 A * | 4/1998 | Echerer et al. | 382/132 |
| 5,805,118 A * | 9/1998 | Mishra et al. | 345/1.1 |
| 6,614,453 B1 * | 9/2003 | Suri et al. | 715/764 |
| 6,728,424 B1 * | 4/2004 | Zhu et al. | 382/294 |
| 6,734,880 B2 * | 5/2004 | Chang et al. | 715/738 |
| 7,020,844 B2 * | 3/2006 | Trevino et al. | 715/772 |
| 7,058,901 B1 * | 6/2006 | Hafey et al. | 715/792 |
| 7,158,692 B2 * | 1/2007 | Chalana et al. | 382/294 |
| 7,162,623 B2 * | 1/2007 | Yngvesson | 713/1 |
| 7,450,747 B2 * | 11/2008 | Jabri et al. | 382/132 |
| 7,657,566 B2 * | 2/2010 | Mathavu et al. | 703/6 |
| 7,668,358 B2 * | 2/2010 | Snoeren et al. | 382/131 |
| 7,715,654 B2 * | 5/2010 | Chefd'hotel et al. | 382/294 |
| 7,747,050 B2 * | 6/2010 | Lau et al. | 382/128 |
| 7,769,216 B2 * | 8/2010 | Doi et al. | 382/128 |
| 7,848,553 B2 * | 12/2010 | Hertel et al. | 382/128 |
| 7,864,994 B2 * | 1/2011 | Fidrich et al. | 382/128 |
| 7,865,004 B2 * | 1/2011 | Moriya | 382/128 |
| 7,885,440 B2 * | 2/2011 | Fram et al. | 382/128 |
| 7,920,152 B2 * | 4/2011 | Fram et al. | 345/661 |
| 7,961,921 B2 * | 6/2011 | Mahesh | 382/128 |
| 7,995,818 B2 * | 8/2011 | Mahesh et al. | 382/128 |
| 8,031,211 B2 * | 10/2011 | Shekhar et al. | 345/648 |
| 2003/0028116 A1 | 2/2003 | Bimbaum | |
| 2004/0109008 A1 | 6/2004 | Sako | |
| 2005/0100136 A1 | 5/2005 | Kawatsu | |
| 2006/0004275 A1 | 1/2006 | Vija et al. | |
| 2006/0030768 A1 | 2/2006 | Ramamurthy et al. | |

OTHER PUBLICATIONS

Vision Tools "MultiView"; MillenTech Systems; http://www.millentech-systems.com/products/multiview/ printed Jul. 6, 2006.

(Continued)

*Primary Examiner* — Long V. Le
*Assistant Examiner* — Bradley Impink

(57) ABSTRACT

A medical imaging system (10) comprises one or more displays (66). A viewer device (86) generates an interactive user interface screen (80) on the display (66), which viewer device (86) enables a user to simultaneously inspect selected image data of multiple patients or multiple images.

17 Claims, 17 Drawing Sheets

OTHER PUBLICATIONS

Analyze Modules; Mayo Clinic; http://www.mayo.edu/bir/Software/Analyze/Analyze1b/printed Jul. 6, 2006.

Vision Tools "3Dview"; MillenTech Systems; http://www.millentech-systems.com/products/multiview/printed Jul. 6, 2006.

* cited by examiner

MULTI-MODALITY MEDICAL IMAGE VIEWING

BACKGROUND

The present application relates to the medical imaging systems and methods. It finds particular application in conjunction with multi-modality systems, such as PET-CT systems. It will be appreciated that the invention is also applicable to the various combinations of SPECT, CT, ultrasound, MRI, fluoroscopy, and the like.

In multi-modality tomographic systems, two or more different sensing modalities are used to locate or measure different constituents in the object space. In the PET-CT system, the PET creates images of high metabolic activity in the body, rather than creating images of surrounding anatomy. CT scans allow doctors to see the internal structures within the human body. Before having a PET-CT scan, the patient receives a dose of a radiopharmaceutical. The pharmaceutical is carried through the blood and concentrates in a particular organ or region and causes radiation to be emitted from the blood and this organ or region. During the scan, tracings of the emitted radiation are detected by the system creating an image of the distribution of the radiopharmaceutical in the patient. The image can show the circulatory system and/or the relative absorption of the radiopharmaceutical in various regions or organs. Integration of the anatomical data from the CT scan with the metabolic data from the PET scan in the PET-CT image gives physicians visual information to determine if disease is present, the location and extent of disease, and track how rapidly it is spreading. The PET-CT system is particularly helpful in difficult-to-treat regions (e.g. head and neck area, mediastinum, postsurgical abdomen) and localization of the treatment area for the patients receiving radiation therapy or chemotherapy.

As each medical imaging modality may provide complementary information on the imaged subject, it is desirable to combine all available information for review. There is a growing demand for a medical imaging review system to be able to handle multiple patients and multiple modalities over a temporally spaced series of imaging sessions. However, the current approach for viewing of the multiple patients is to load patients one at a time, which is cumbersome from a workflow standard point of view and also renders patient comparison difficult if not impossible.

Another problem arises in handling multiplicity of patients and modalities. One problem, or example, is the registration of images from multiple modalities or the same modality over multiple imaging sessions. Current methods allow handling of only few images with the assumption that the first volumetric image is fixed. Another problem is in providing support when conflicting requirements due to different needs exist. One approach is to provide customizable display protocols. However, the customizable display protocols make a tightly integrated viewing environment difficult to define and implement.

The present application provides new and improved methods and apparatuses which overcome the above-referenced problems and others.

SUMMARY

In accordance with one aspect, a medical imaging system which comprises one or more displays is disclosed. A viewer device generates an interactive user interface screen on the display, which viewer device enables a user to simultaneously inspect selected image data of multiple patients or multiple images.

In accordance with another aspect, a medical imaging method is disclosed. An interactive user interface screen is generated on a display. Selected image data of multiple patients or multiple images is simultaneously inspected on the display.

One advantage is that multiple images can be simultaneously reviewed in a side to side comparison.

Another advantage is that unlimited support of customer display protocols is provided.

Another advantage resides in simplicity of image alignment.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
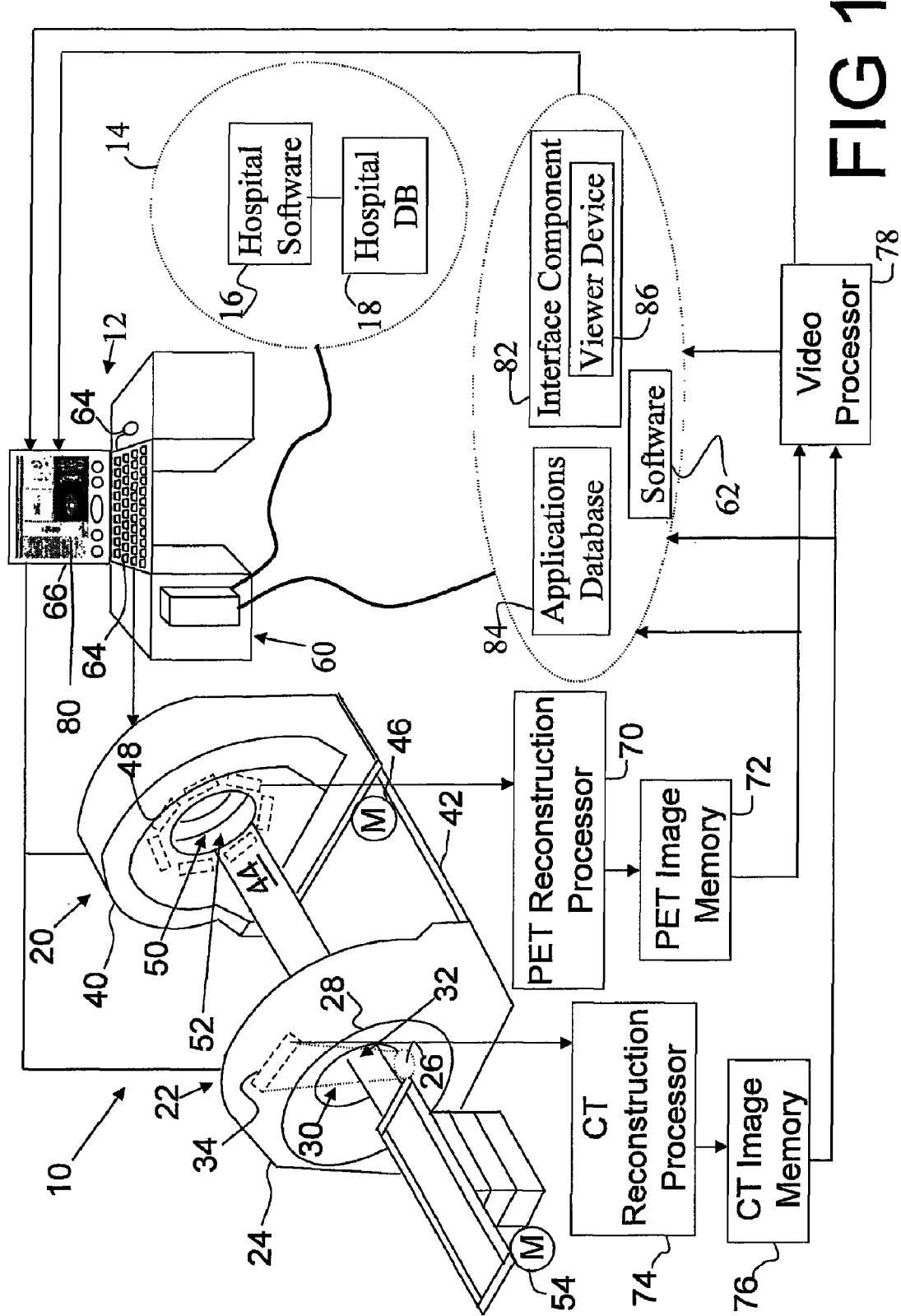
FIG. 1 is a diagrammatic illustration of an imaging system.

With reference to FIG. 1, an operation of an imaging multi-modality system 10, which, for example, include any combination of known imaging modalities, is controlled from an operator workstation 12 which is coupled to a hospital network 14. The hospital network 14 includes associated hospital software 16 and a hospital records database 18. The workstation 12 may be hardwired to the network 14 or may communicate with it wirelessly. In one embodiment, the workstation 12 communicates with other hospital workstations or computers, which are connected to the hospital network 14, enabling the images and patient records to be forwarded to the appropriate hospital personnel and displayed on associated monitors. Of course, it is contemplated that imaging system 10 is a stand alone system without network connections.

The multi-modality system 10 includes a first imaging system, preferably a functional modality, preferably, a nuclear imaging system 20, and a second imaging system, such as a computed tomography (CT) scanner 22. The CT scanner 22 includes a non-rotating gantry 24. An x-ray tube 26 is mounted to a rotating gantry 28. A bore 30 defines an examination region 32 of the CT scanner 22. An array of radiation detectors 34 is disposed on the rotating gantry 28 to receive radiation from the x-ray tube 26 after the x-rays transverse the examination region 32. Alternatively, the array of detectors 34 may be positioned on the non-rotating gantry 24. Of course, other imaging systems are also contemplated.

The functional or nuclear imaging system 20, preferably, includes a positron emission tomography (PET) scanner 40 which is mounted on tracks 42. Of course, SPECT and other imaging systems are also contemplated. The tracks 42 extend in parallel to a longitudinal axis of a subject support or couch 44, thus enabling the CT scanner 22 and PET scanner 40 to form a closed system. A moving means 46, such as a motor and a drive, is provided to move the PET scanner 40 in and out of the closed position. Detectors 48 are arranged around a bore 50 which defines an examination region 52. In the PET system, the detectors 48 are preferably arranged in a stationery ring, although rotatable heads are also contemplated. In the SPECT system, the detectors 48 are preferably incorporated into individual heads, which are mounted for rotational and radial movement relative to the patient. A couch moving means 54, such as a motor and a drive, provides a longitudinal movement and vertical adjustment of the couch 44 in the examination regions 32, 52.

With continuing reference to FIG. 1, an operator, user or imaging technician performs a scan using the workstation 12 which includes a CPU processor or hardware device 60 and a software component or means 62 for carrying out the image processing functions and operations. The workstation 12 preferably includes one or more input devices 64 (e.g., a computer keyboard, mouse, etc.), and one or more monitors or displays 66. The user, via the input devices 64, can selectively control the workstation 12 and/or the entire imaging system 10. The couch 44, which carries a subject, is moved by the couch moving means 54 into the examination region 52 for a PET image to be generated by the PET scanner 40. Electronic data is reconstructed into a PET image by a PET reconstruction processor 70 and stored in a PET image memory 72. The couch moving means 54 moves the couch 44 to position the couch carrying the subject in the CT scanner examination region 32, where a CT image is taken. More particularly, the couch 44 with the subject is moved to the position in the CT examination 32 region that is geometrically and mechanically predicted as being the same as its imaged position in the PET imaging region 52. Electronic data is reconstructed into a 3D CT image by a CT reconstruction processor 74 and stored in a CT image memory 76.

The PET and CT images are aligned, registered, fused or manipulated in any other appropriate way, after which the image data is appropriately formatted by a video processor 78 for display on the monitor 66.

The operator or user controls display of images by using an application interface screen or screens 80 which are incorporated into the workstation 12 and displayed on the monitor 66. An interface component, processor, or means 82 controls the application interface 80. The operator uses the input device, such as a keyboard or mouse 64, to interact with an applications database 84 by navigating the application interface screens 80.

Figure 2:
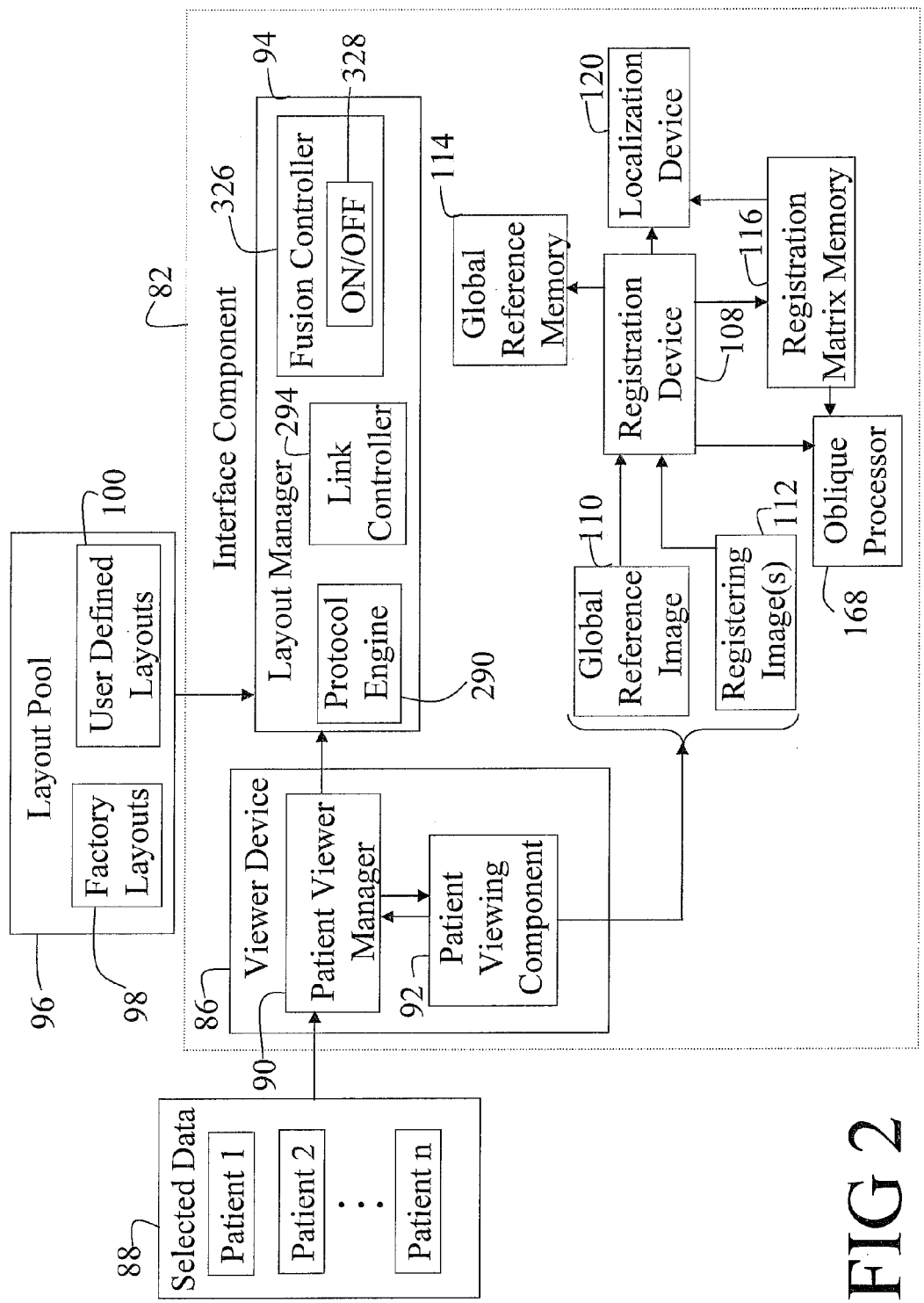
FIG. 2 is a diagrammatic illustration of a detailed portion of the imaging system.

With continuing reference to FIG. 1 and further reference to FIG. 2, a viewer algorithm, device or means 86 allows the user to view, navigate and compare images of multiple patients. For example, the user selects multiple patient data to review and/or compare patients via the interface screens 80. Selected patient data 88 is passed to the viewer device 86 which then creates a patient viewer manager component 90 and passes the data to it.

The patient viewer manager 90 maintains the selected image data for each individual patient. More specifically, the patient viewer manager 90 keeps track of which patients are currently being viewed, launches any new patient for viewing in any order, closes a patient in viewing, and tabs all patients in viewing or tiles all patients in viewing for direct side by side comparison. The patient viewer manager 90 can launch a patient by name, or launch a patient before or after a given patient. If the patient is already launched, it is brought up to the front. If the patient's record is not launched or opened, a new launch is created.

A patient viewing component, algorithm, device or means 92 is responsible for a given patient viewing. The first patient on the list is chosen for viewing automatically at start-up time. More than two patients can be displayed in a tiled format which can be in a single display monitor or cross multiple monitors, for direct side by side comparison.

The navigations among the patients in viewing are done through clicking on a patient tab or selecting that patient from a graphical user interface control (a list control). The patient data is loaded into the application on-demand to reduce the memory usage. However, it is also possible to load all data if the total data does not consume much memory or if the memory with a proper size is available. In this manner, multiple patients are viewed directly in a single integrated environment.

Figure 3:
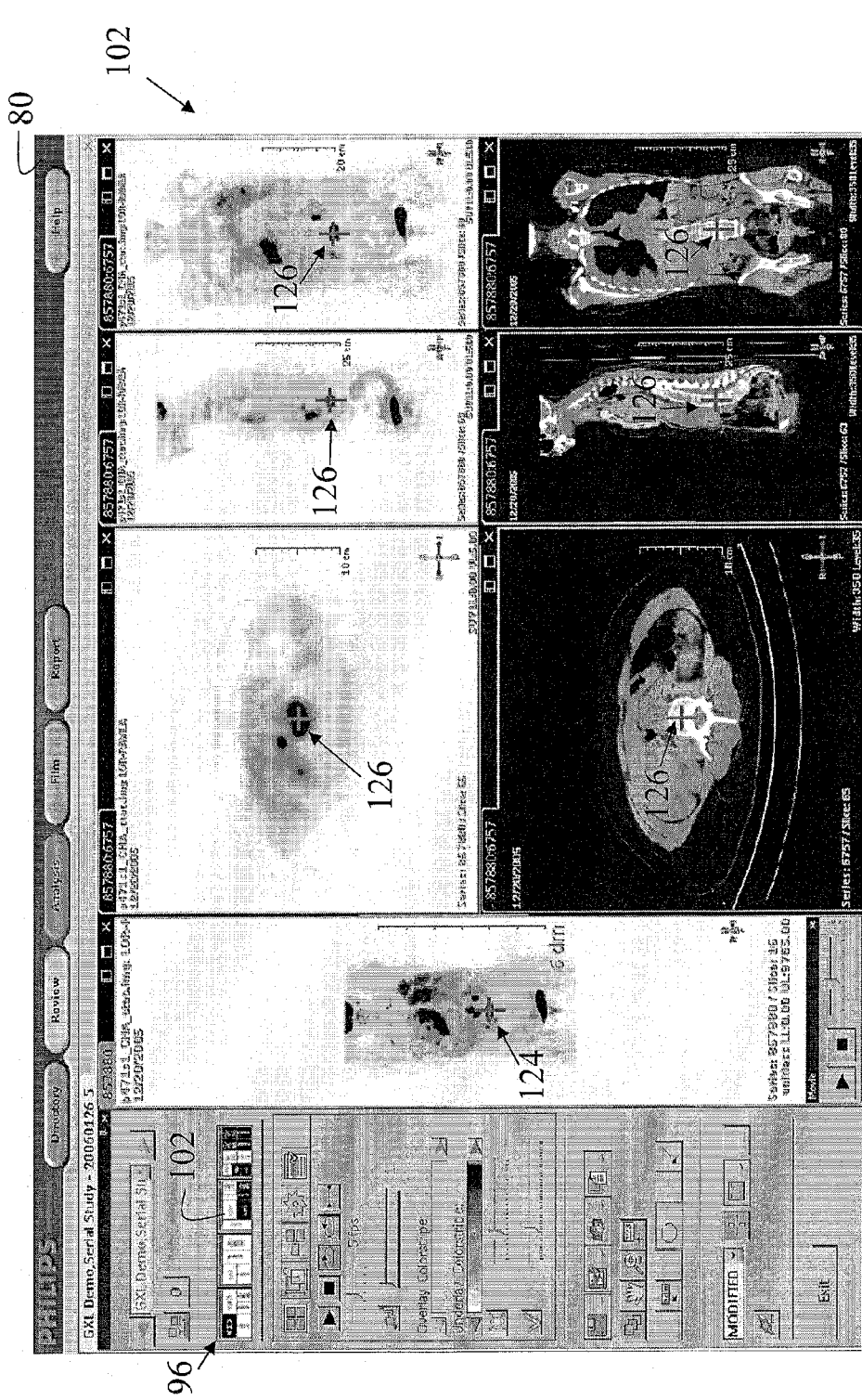
FIG. 3 is an image of a user interface screen showing a layout.
Figure 4:
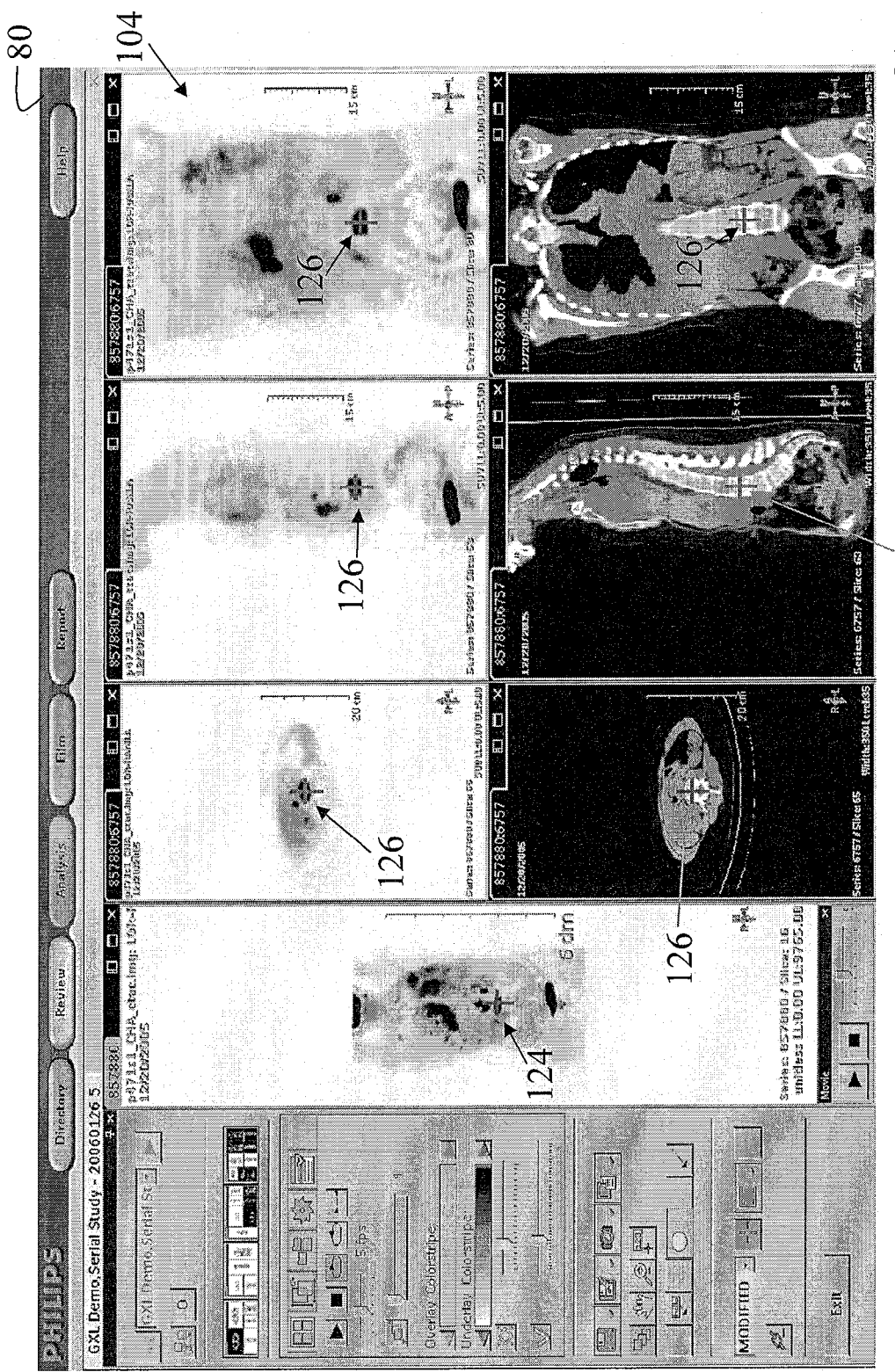
FIG. 4 is an image of a user interface screen showing another layout.

With continuing reference to FIG. 2 and further reference to FIG. 3, a layout manager, component, device, algorithm or means 94 manages layouts. More specifically, the layout manager 94 maintains a collection of layouts or layout pool 96. The layouts are obtained from embedded resources for factory layouts 98 and files for user defined layouts 100. Given a particular set of selected patient image data for reviewing, a predefined startup layout 102 is determined by consulting a preference setting. The user may switch to a different layout yet to be created or visited previously during a reviewing session. The user may modify a predefined layout as shown in FIG. 4 and save the modified layout 104. The user may also start from scratch, define his or her own layout, set it as the preferred one for a particular given set of image data, and use it in subsequent viewing sessions. For the currently displayed layout, the user may replace one image data with a different image data. The replacing image data can be displayed in the context of the replaced data, e.g. in the same layout. Alternatively, the best matching layout is found and launched. All images are displayed with the same viewing context.

With continuing reference to FIG. 2, a registration component, device, algorithm, processor or means 108 selects a global reference image 110 and registers or aligns images 112 with one another with respect to the global reference image 110. Any number of images can be managed and registered at a single time. Any image can participate in the registration as either a reference image or a floating image. More specifically, if a single image is selected for viewing, the image is viewed in its own coordinate system. When two or more images are selected for viewing, one image is selected as a reference image and the rest of the images is designated as floating image(s). The floating images are shifted and rotated to match the reference image. The individual relation of each floating image to the reference image is computed based on the relation of each image to the global reference as discussed in detail below. The initial registration relation is determined on the as needed basis. In the registration that involves multiple images, the registration relation is propagated to other images in a well-controlled manner.

For example, when a group of images (including the case where only one image is selected) is selected for viewing for the first time, the registration device 108 selects the first volumetric image in the group as the global reference 110 (once the global reference is determined, it will not change). A global reference coordinate system, which defines a common frame of reference, is stored in a global reference memory 114.

When an image 112 is selected for viewing, the registration device 108 determines and stores a registration matrix (or parameters) for this particular volumetric image with respect to the global reference and stores the registration matrix in a registration matrix memory 116.

In one embodiment, the registration device 108 compares the frame of reference of each image to the common frame of reference, e.g. frame of reference of the global reference image. If the image has the same frame of reference unique identification (FoR UID) as that of the global reference and there is no other information to overwrite that, the registration matrix is identity. If the image and the global reference have different FoR UID and the registration is not known a priori, the registration device 108 aligns the volume centers of the two images and propagates the resultant registration matrix to all other volumetric images that share the same FoR UID as the image under registration. As a result, registrations of such images to the global reference image do not need to be determined. If the registration between the image and the global reference is known a priori, the registration device 108 propagates the determined registration matrix to all other volumetric images that share the same FoR UID as the image under registration. The registrations of such images to the global reference image do not need to be determined. In this manner, registrations of multiple images are simplified.

The registration of the global reference can be changed. Any change is interpreted as a change with respect to its original coordinate system. The registration of any image with respect to the global reference is interpreted with respect to the original coordinate system of the global reference.

As an alternative, the global reference can be duplicated or copied to be registered to other images as a floating image. As another alternative, the registration matrices of each image can be determined in a single step rather than on-demand basis.

Figure 5:
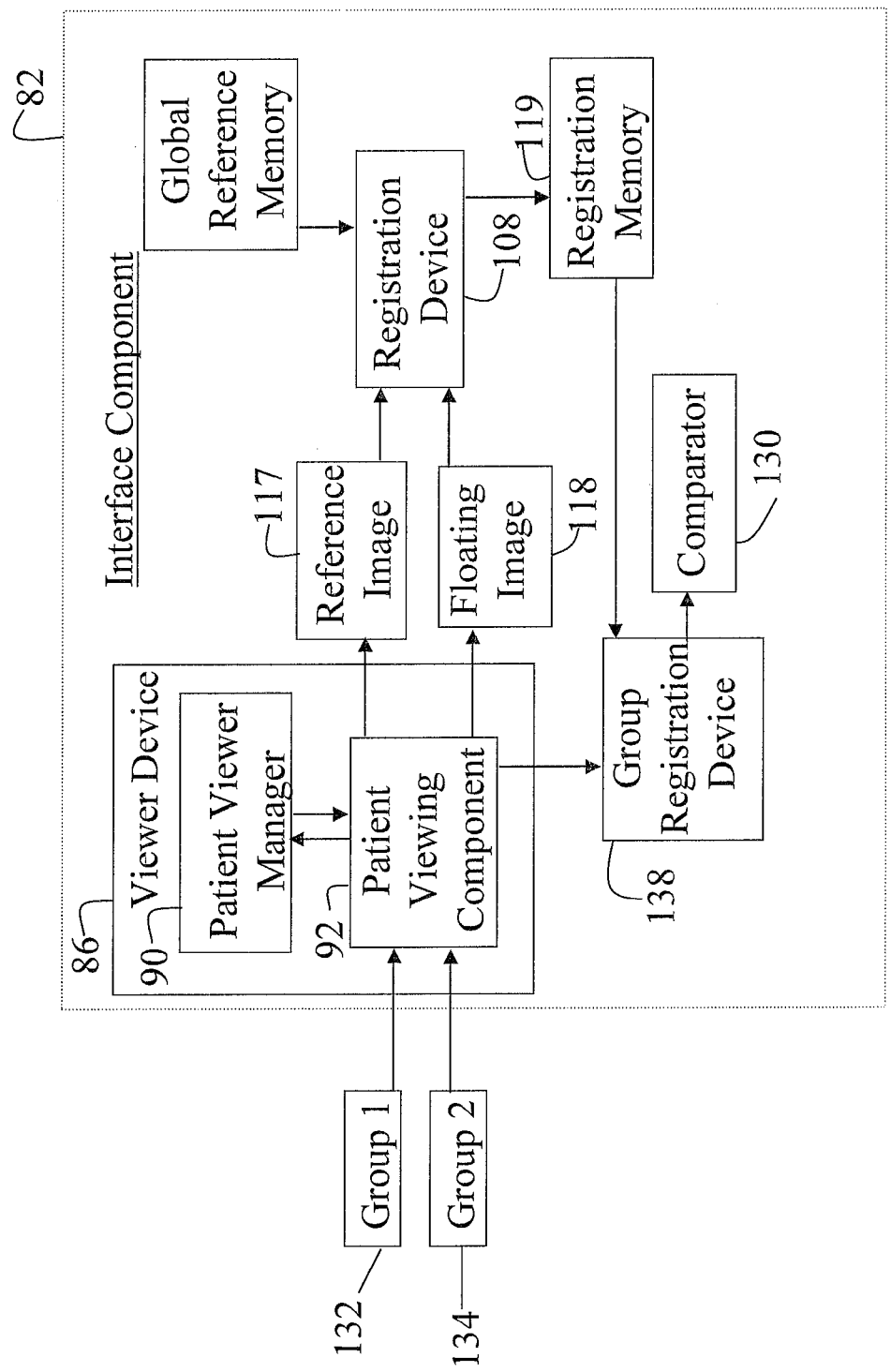
FIG. 5 is a diagrammatic illustration of another detailed portion of an imaging system.

With continuing reference to FIG. 2 and further reference to FIG. 5, the registration processor 108 computes a relative registration relation $M_{r1r2}$ between first and second or reference and floating volumetric images 117, 118 as:

$$M_{r1r2} = M_{r1}^{-1} M_{r2}, \text{ where}$$

$M_{r1}$ is the registration of the first image with respect to the global reference; and
$M_{r2}$ is the registration of the second image with respect to the global reference.

The relative registration $M_{r1r2}$ between the reference and floating volumetric images 117, 118 is stored in a registration memory 119.

When the relative registration $M_{r1r2}$ of the floating image 118 with respect to the reference image 117 is changed due to any reasons (manual registration, automatic registration, etc), the equivalent change with respect to the global reference image 110 is computed and recorded. The same registration is propagated to other images in a controlled manner.

The registration $Mr_2$ of the floating image 118 with respect to the global reference is:

$$M_{r2} = M_{r1} M_{r1r2}.$$

If the reference image and floating image have different FoR UID, the registration $M_{r2}$ of the floating image with respect to the global reference is propagated to all other volumetric images that share the same FoR UID as the floating image under concern. If the FoR UID is not present, it is considered as a mismatch.

If the reference image and floating image have the same FoR UID, to correct the motion between CT and PET acquisition, for example, the registration $M_{r2}$ of the floating image with respect to the global reference is propagated to all other images that share the same FOR UID as the floating image under concern and have the same modality as the floating image.

In this manner, a global reference volumetric image 110 is introduced and all other volumetric images are registered to such virtual global reference. There is no limit on the number of volumetric images the registration device 108 can handle and register at a single time. The coordinate system of the global reference is not fixed. The global reference can participate in the registration as a floating image with respect to other images (the coordinate system of the global reference before registration is used as global reference coordinate system and thus is virtual). The registration relation between any two volumetric images is computed from their respective relation with the global reference. The individual relation to the global reference can be decided inside the same application or inferred from outside information (same or different frame of reference unique identification (FoR UID), or DICOM spatial registration object). The global reference is intelligently selected. For example, in the case of mixed volumetric and non-volumetric images, the global reference is not set until a first volumetric image is selected for viewing. Likewise, the individual registration with respect to the global reference is not determined until the image is selected for viewing. If there is no pre-determined registration between the global reference and the image under concern, the two centers of the volumetric images are aligned and that alignment relation is set as the initial registration that can be overwritten later if necessary. Moreover, the so-determined initial registration is propagated to other volumetric images if their relations to the image under concern are known.

When multiple floating images are registered to the same reference image, the registrations with respect to the reference image can be updated as a group with the option that each individual image can be either updated or not updated.

With continuing reference to FIG. 2, a localization device, algorithm, processor or means 120 uses a maximum intensity projection (MaxIP) of the PET image to update other image planes such as transverse, sagittal, and/or coronal images. More specifically, the user selects a point of interest, for example, by clicking on a point in the image with the mouse. The localization device 120 computes the exact location of the selected point and uses this point's 3D coordinates to update all other image planes. The clicked point is computed in the original coordinate system and transformed to the common registered coordinate system. If there are more than two images which are registered and displayed, the localization device 120 allows the registered and fused images to be updated properly. Optionally, the MaxIP image, transverse, sagittal, and/or coronal images of other volumetric images can be displayed at the same time and can be fused with the corresponding transverse, sagittal, or coronal images. As a further option, the MaxIP image can be fused. In the case of MaxIP fusion, the user has the option to specify which MaxIP image from the correlation to be used from this addresses the case in which two different physical locations contribute to the same point in the MaxIP images. In the case that the clicked point is from a regular two-dimensional image plane (transverse/sagittal/coronal), a point in the MaxIP image is also identified where the maximum intensity pixel and the clicked point are in the same projection line.

Figure 6:
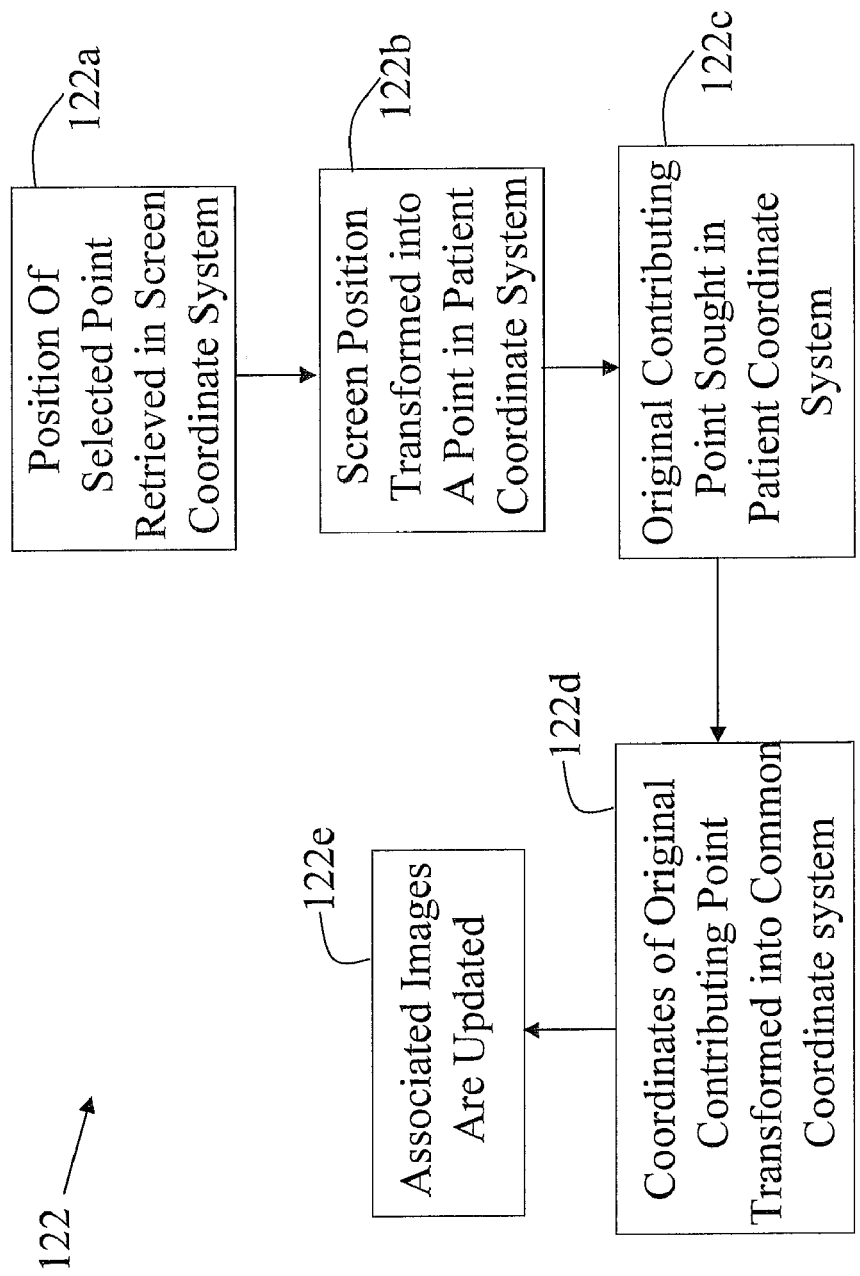
FIG. 6 is a flow chart of a localization process.

More specifically, with particular reference to FIG. 6, the localization device 120 performs a localization process 122 after the user selects a point on the MaxIP image. In step 122*a*, the position of the clicked point is retrieved in the screen coordinate system. In step 122*b*, the screen position is transformed into a point in patient coordinate system by taking into account the image position and image orientation vectors. In step 122*c*, the original contributing point in patient coordinate system is sought. Optionally, the information can be stored and no further computation is needed. In step 122*d*, the coordinates found in step 122*c* are transformed into a common coordinate system (i.e. of the global reference image). In step 122*e*, the coordinates in the common coordinate system are used to update all associated images. E.g., the transverse image at the same z position is displayed.

With reference again to FIGS. 3 and 4, a selected point of interest 124 is illustrated by a cross. The selected point of interest 124 is propagated to all associated images to identify corresponding points of interest 126.

With reference again to FIG. 5, a comparator 130 compares temporal studies or groups 132, 134 of selected images. More specifically, the user selects different groups such as first and second groups of images 132, 134 for comparison via the interface screen 80. For example, if two or more DICOM study objects are selected, the volumetric images in each study form a group. Volumetric images can also be directly selected to form groups. The user can start with one group and use combinations of keys and mouse or other devices to select more groups. A two-dimensional array is used to represent selected groups, in which each row is a group. One of the volumetric images, for example a first image in the group, is selected as the reference image 117, for example, automatically or manually. The rest of the images of the group are designated as floating images 118. All floating images 118 in the same group are registered to the reference image 117 in the same group.

Within a group, the floating image has to be informed which image is the reference image; and the reference image has to be informed it is a reference image.

After the comparison groups 132, 134 are formed, the comparison groups 132, 134 can be displayed independently. A group registration device, algorithm, means or processor 138 determines a linking relation between groups that is used in subsequent reviewing. The registration can be established in at least two different ways: (1) the crude registration and (2) the precise registration.

Figure 7:
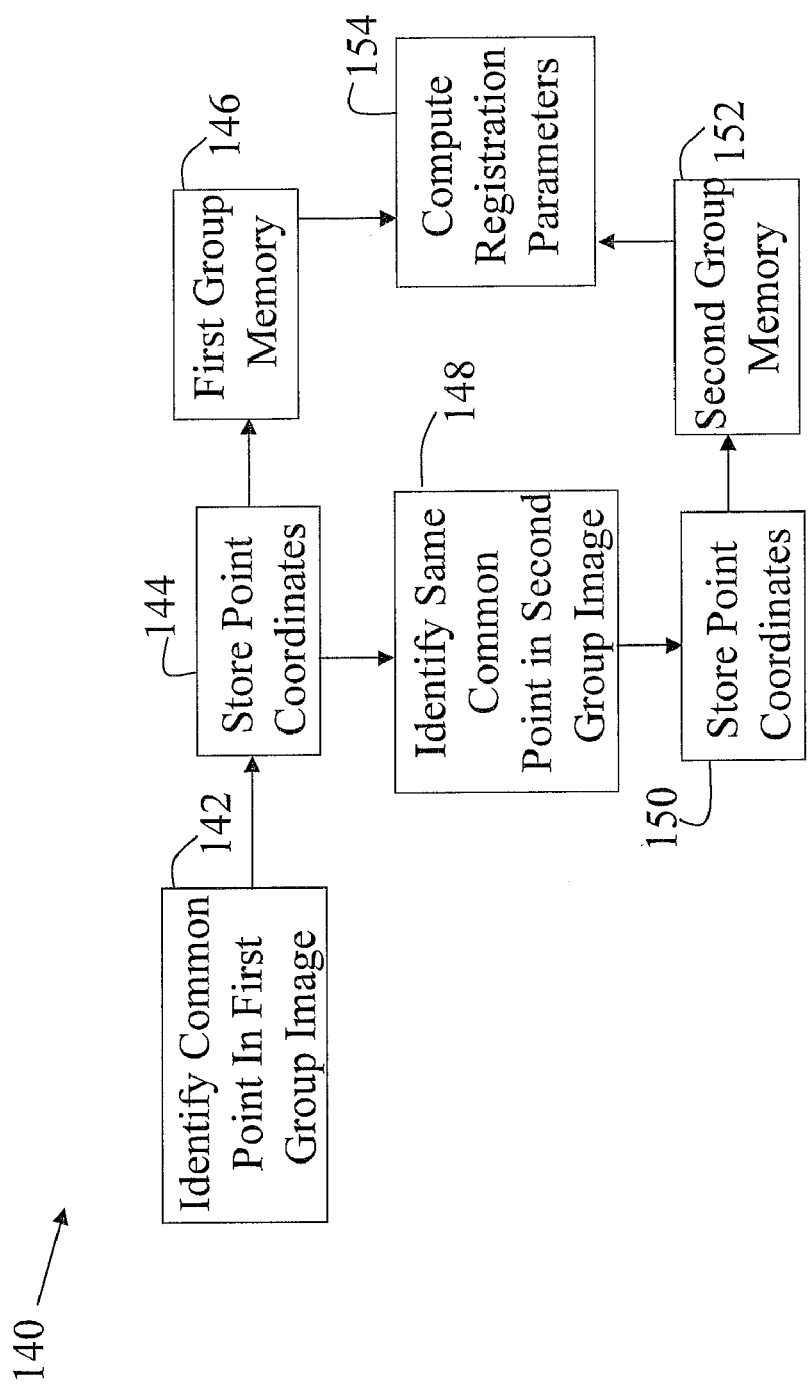
FIG. 7 is a flow chart of a crude registration of comparison groups.

With continuing reference to FIG. 6 and further reference to FIG. 7, the group registration processor 138 determines the crude registration in a crude group registration process 140. In step 142, a point correlation (triangulation) is used to identify a common point (hot spot, internal mark, or external mark) in any volumetric image in the first group 132. For example, the user clicks on the point of interest in one of the images of the first group 132. Step 142 can be performed multiple times. Position of the identified point is stored 144 in a first group memory 146. In step 148, the point correlation is similarly used to identify the same common point in any volumetric image in the second group 134. For example, the user clicks on the similar point in one of the images of the second group 134. Step 148 can be performed multiple times. Position of the identified point is stored 150 in a second group memory 152. Of course, step 148 can be performed on more than one group.

Alternatively, several common points can be identified in each group 132, 134 to improve the registration accuracy. The positions of the points are stored in a corresponding first or second group memory 146, 152.

After the common points in all groups are identified, the group registration processor 138 retrieves the stored positions from the first and second group memories 146, 152 and the registration is computed 154. The process 140 can be initialized with a clicking on a graphical (button) control. More hue can be provided once the relation is computed. Only the relation with respect to the first group is computed regardless of a number of groups selected.

If there is only one point identified in each group, only translation relation between two groups is considered, which is given by the differences between their x/y/z coordinates. If two points are identified in each group, translation (or translation and one rotation) relation between two groups is considered. If more than three (inclusive) points are identified, the relation can be found by the technique used in conjugate-point based registration. It is not required to select the same number of points in each group.

Figure 8:
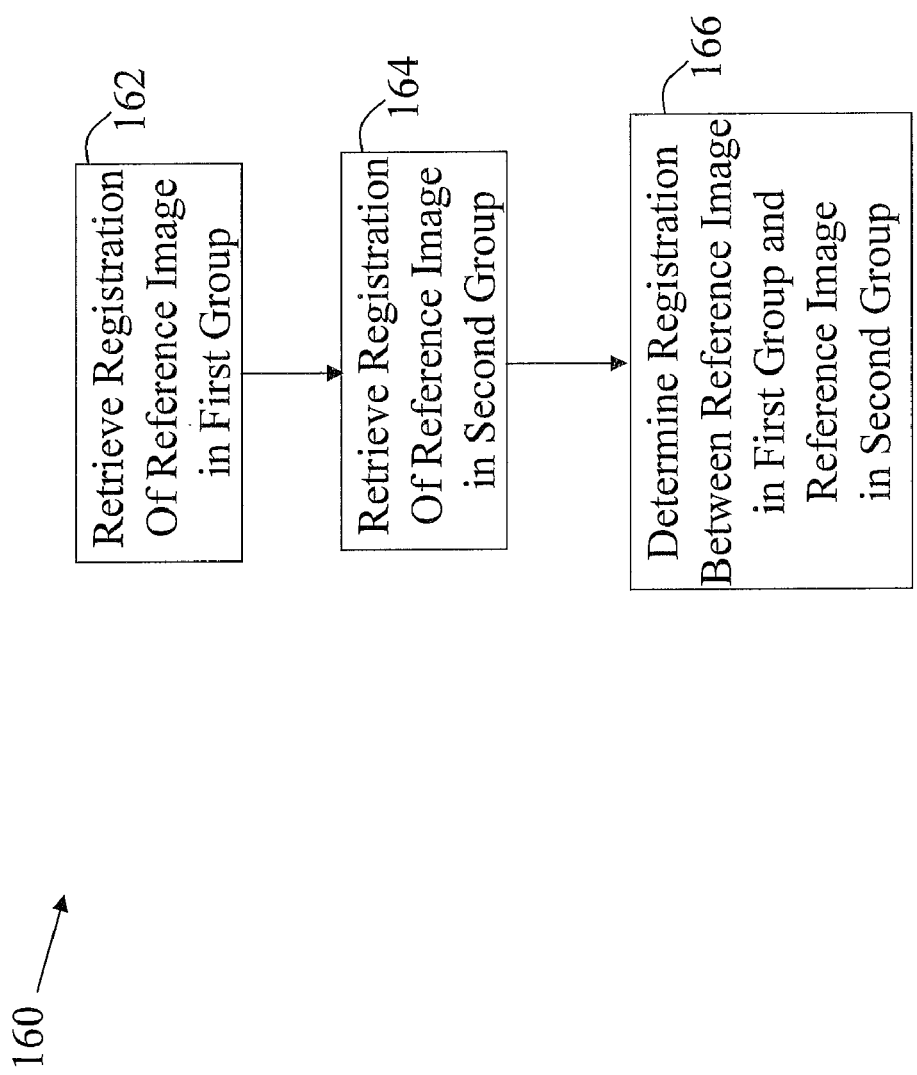
FIG. 8 is a flow chart of precise registration of comparison groups.

With continuing reference to FIG. 6 and further reference to FIG. 8, the group registration processor 138 determines 160 the precise registration between groups by using registration between two studies (one volumetric image from each study group) and linking the groups by this precise relation. For example, a first image in each group is selected as the reference image. The registration $M_{r1}$ of the reference image 117 of in the first group 132 with respect to the global reference 110 is retrieved 162. The registration $M_{r2}$ of the reference image of the second group 134 with respect to the global reference 110 is retrieved 164. The registration $M_{r1r2}$ between the reference image in the first group 132 and the reference image in the second group 134 is determined 166 as:

$$M_{r1r2}=M_{r1}^{-1}M_{r2},$$

where $M_{r1}$ is the registration of the first reference image with respect to the global reference; and
$M_{r2}$ is the registration of the second reference image with respect to the global reference.

The registration $M_{r1r2}$ is used as the registration between the two groups 132, 134. For other groups if any, only the relation with the first group 132 is maintained which is determined in the same manner. Alternatively, all pairwise relations can be maintained and used. Once the group relation is established, the same relation is used to link the localization points in the reference images of each group. Whenever the localization point changes in any group, the corresponding point in other groups are computed using the linking relation established early and the computed point is set to their groups, which triggers the update within the group.

Figure 9:
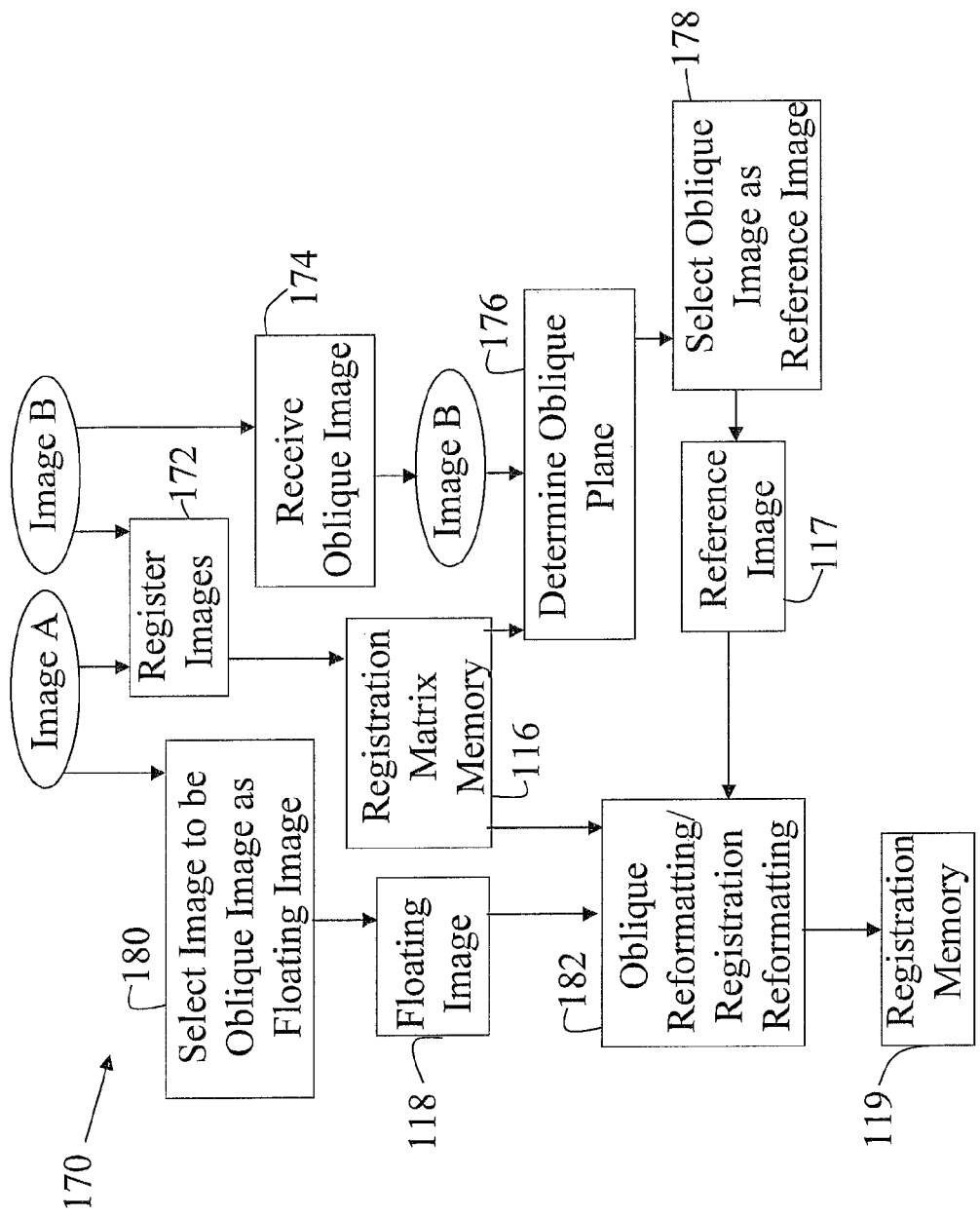
FIG. 9 is a flow chart of a registration reformatting which results in oblique reformatting.

With reference again to FIG. 2 and further reference to FIG. 9, an oblique processor, device, algorithm or means 168 performs 170 a registration reformatting to do an oblique reformatting to one of the two images. For example, two volumetric images A and B are registered with respect to the global reference and the registration matrix 116 is available. Alternatively, images A, B share the same FoR UID. Alternatively, images A, B are registered 172, either manually or automatically, inside or outside the same application and the registration matrix is available. Alternatively one can directly set the registration parameters using the provided registration numerical values.

In step 174, an oblique image is received. For example, at least one of the images A, B is oblique. The image can be oblique when the image is loaded from disk. Alternatively, the image is made oblique reformatted within the same application. As a further option, the image itself is not oblique directly, but the oblique parameters are set and used.

In step 176, an oblique plane is determined. For example, if the oblique images are loaded from the disk directly, the oblique plane is determined from the image orientation vectors. The cross product of those two vectors gives a third vector. The name of the oblique plane (oblique transverse/sagittal/coronal) can be determined by the information coded in the image if present; otherwise, it is determined by comparing the image orientation vectors with respect to the standard x/y/z axes, and if it is closest to the transverse (sagittal or coronal) plane, it is oblique transverse (sagittal or coronal). The comparison is done on the summation of squared inner products between normalized vectors and the larger, the closer. In the comparison, the directions of those vectors are ignored. Denote the three oblique vectors as u, v, and w, which are closest to the x, y, and z-axes respectively. Generally, the directions of the u, v, and w vectors point to the directions of positive x, y, and z-axes respectively; if not, they are negated.

If the oblique images are not loaded from disk files, but generated, then the three oblique vectors can be decided in the same fashion.

A set of geometric information is generated for oblique slice creation, which includes the image orientation vectors, the number of slices, the center of the generated slices, the physical extent of the generated slices, and the number of pixels and pixel physical sizes for the slices. The image orientation vectors are determined by the name of the oblique planes. For example, if an oblique transverse view is requested, two vectors u and v are used. If an oblique sagittal view is requested, y and w are used. If an oblique coronal view is requested, then w and x are used.

In steps 178, 180, the oblique image (Image B) is selected as a reference image 117 and an image to be oblique (Image A) is selected as a floating image 118. The floating image 118 is automatically oblique reformatted 182 due to the registration reformatting. Particularly, the generated geometric information is used to create oblique slice for the image A. The geometric information can be used directly. As an alternative, the center of the generated slices, the physical extent of the generated slices, and the number of pixels and pixel physical sizes for the slices can vary. When generating the slices for a different image, the registration of this image with respect to the reference image, on which the geometric information (mainly orientation vectors and image position) is specified, is taken into account. This process is called registration reformatting. User can optionally save the secondary reformatted images in any oblique plane should it be available.

In this manner, a new workflow concept utilizes the registration reformatting to do the oblique reformatting, which avoids the manual or automatic oblique reformatting operation on associated images. In the fusion display, the oblique planes of the oblique image (reference) are used rather than the conventional transverse/sagittal/coronal image planes, i.e. the oblique transverse/sagittal/coronal image planes are used. Due to the registration reformatting, the other (floating) image is automatically oblique reformatted to have the same image planes as the oblique (reference) image. This way, the tedious manual oblique reformatting on the (floating) image can be avoided or the automatic oblique reformatting becomes unnecessary, which often generates a different set of oblique parameters.

Figure 10:
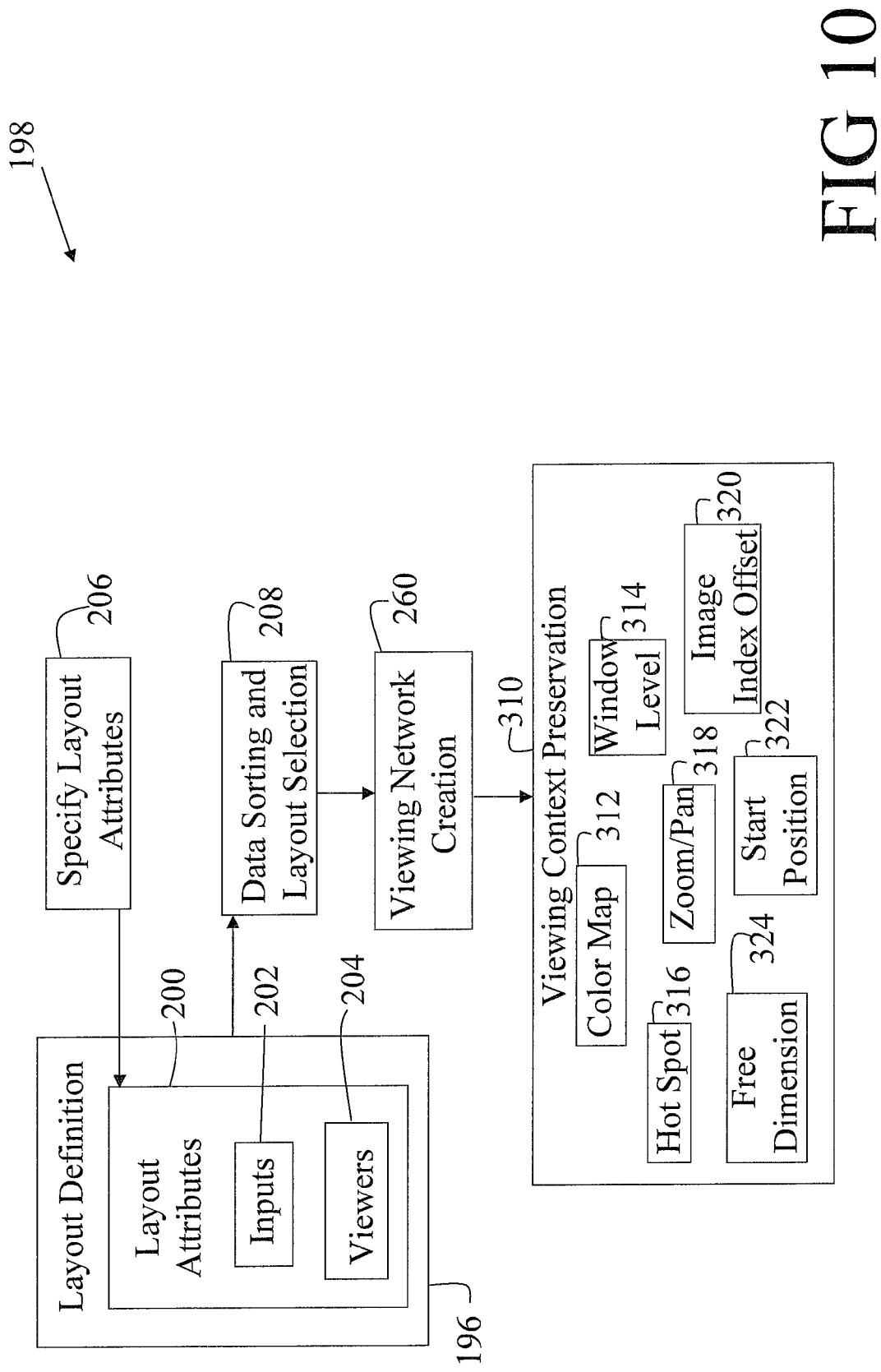
FIG. 10 is a flow chart of a layout definition.

With continuing reference to FIG. 2 and further reference to FIG. 10, the layout manager 94 defines and/or creates a layout definition 196 in step 198, in which layout attributes 200, such as data inputs 202 and viewers 204 are specified 206, and data is associated with the viewers 204. The layout definition 196 can be defined in any format of a text file or a data object as long as it can be easily manipulated. An exemplary XML format is:

```
<name>Axial-comparison-AllF</name>
<description>AxialComparison</description>
<writable>false</writable>
<favoriteRating>101</favoriteRating>
<inputs>
    <Characteristics>
        <inputReference>Input1</inputReference>
        <modality>Anatomical</modality>
    </Characteristics>
    <Characteristics>
        <inputReference>Input2</inputReference>
        <modality>FunctionalAnatomical</modality>
    </Characteristics>
</inputs>
<ViewerCfgs>
    <ViewerCfg>
        <width>50</width>
        <height>100</height>
        <x>0</x>
        <y>0</y>
        <viewerType>MPR</viewerType>
            <fusionState>Underlay</fusionState>
        <underlay>
            <inputReference>Input1</inputReference>
        </underlay>
        <overlay>
            <inputReference>Input2</inputReference>
        </overlay>
        <orientation>Transverse</orientation>
        <zoomFactor>1.3</zoomFactor>
    </ViewerCfg>
    <ViewerCfg>
        <width>50</width>
        <height>100</height>
        <x>50</x>
        <y>0</y>
        <viewerType>MPR</viewerType>
            <fusionState>Overlay</fusionState>
        <underlay>
            <inputReference>Input1</inputReference>
        </underlay>
        <overlay>
            <inputReference>Input2</inputReference>
        </overlay>
        <orientation>Transverse</orientation>
        <enableCine>false</enableCine>
        <zoomFactor>1.3</zoomFactor>
    </ViewerCfg>
</ViewerCfgs>
</Layout>
```

Such exemplary layout defines two inputs. A first input ("Input1") looks for any anatomical volume series. A second input ("Input2") looks for any supported volume series, which are defined in a modality field. The value of the modality field can also be very specific, for example, MR, CT, PET, SPECT, SC (secondary capture), etc. The exemplary layout next defines two viewers ("ViewerCfg"), which have fusion capability. The viewers show transverse image orientation: one viewer is showing underlay image and the other viewer is showing overlay image as the starting viewing option. The layout manager 94 can use this file as an input, in conjunction with the selected series and a set of built-in linking rules, to build a complete specification. The layout definition 196 is, of course, scalable to include multiple inputs, multiple viewers with different types, and different viewer configurations. Tables 1-3 below explain how to configure each attribute 200 of a layout definition.

TABLE 1

Layout

| Attribute | Type | Description |
| --- | --- | --- |
| writable | bool | 0: this layout is read only; 1: layout can be overwritten, and can be removed. |
| name | string | Layout name is served as ID. The layout name is unique among all layouts defined by one physician. The layout name/layout icon name/layout file name are the same. |
| description | string | Layout description is used as tool tip and item display on preference page. |
| favoriteRating | int | A score. The higher the value, the better chance the layout will be selected when multiple layouts match a same query. |
| ViewerCfgs | IList | A list of all viewer configurations. |
| inputs | Characteritics[ ] | Characterized data inputs. Each input forms a query to all selected data from application data model (a software component that is responsible for packaging and reformatting image data for display). |

TABLE 2

ViewerCfg

| Attribute | Type | Description |
| --- | --- | --- |
| Name | String | Viewer name, which is normally generated by layout manager at runtime if this is not specified. It is used as a node name by a protocol engine to associate with a viewer. |
| Width | int | Width of tab container holding the viewer |
| Height | int | Height of tab container holding the viewer |
| X | int | X location of the tab container holding the viewer |
| Y | int | Y location of the tab container holding the viewer |
| screenIndex | int | 0 - main monitor, 1 - second monitor |
| viewerType | ViewerType | The exemplary values include Basic2D MPR MIP CardiacOblique BrainOblique Different viewer type means different default viewer configuration. For example, for basic 2D viewing, we do not provide fusion capability for this viewer. For MIP (maximal intensity projection) viewer, we do not provide any ROI measurement tool. For CardiacOblique viewer and BrainOblique viewer, we provide some specialized image interactors. |
| underly | Characteristics | Used to refer to which input source is used for the underlying data view. For example, it is a query among all layout inputs. |
| overlay | Characteristics | Used to refer to which input source is used for the superimposed data view. For example, it is as a query among all layout inputs. |
| orientation | ImageOrientation | Values include Any (Basic2D, MIP) Transverse (TSC display) Sagittal (TSC display) Coronal (TSC display) |
| transformedStage | TransformedStage | Values include NotTransformed (default) |

TABLE 2-continued

| | ViewerCfg | |
|---|---|---|
| Attribute | Type | Description |
| | | Intermediate1<br>Transformed<br>Any values other than NotTransformed are only meaningful for oblique utility layouts. |
| columns | unit | Rows of tiles in the viewer |
| rows | unit | Columns of tiles in the viewer |
| enableCine | bool | This flag indicates if cine should be enabled when the viewer is created. |
| zoomFactor | float | Zoom factor with which the viewer should initially apply to images. If it is not specified, then default 1 will be used. |
| viewerConfigurationClass | string | This attribute allows user to specify his/her own viewer configuration class, which is normally done by layout manager automatically based on viewer type. |
| extraActions | string[ ] | This attributes allows user to instruct layout manager to execute canned actions specified here after a viewing network is established. |

TABLE 3

| | Characteristics | |
|---|---|---|
| Attribute | Type | Description |
| name | string | Unique string used to identify data view generated from this input. It is generated internally by protocol builder |
| inputReference | InputIndex | Values include<br>None<br>Input1<br>Input2<br>Input3<br>Input4<br>Input5<br>Input6<br>—<br>ALL<br>This attribute keeps tracking the original input index. With this macro, we can search all inputs available that meet the criterions presented in Characteristics data object. |
| modality | Modality | Values include supported modality:<br>Any --- any modality including secondary capture,<br>FunctionalAnatomical - any volume<br>Functional - any functional volume such as PET and SPECT,<br>Anatomical - any anatomical volume, PET, CT, MR, SPECT |
| method | Method | Value include<br>Any (default)<br>Diagnostic (CT)<br>LowDose (CT)<br>CTAC (PET)<br>NonAC (PET) |
| contrastAgent | ContrastAgent | Enumeration type. Value include<br>Either (default)<br>NonContrast (not contrast)<br>Contrast (contrast enhanced) |
| groupIndex | Int | It is used in group comparison. It indicates which group this input belongs to. Default value is 0 if it is not specified. |
| ImageType | string[] | Array of strings requiring all image types in this array to be present in order for an NM image to be matched. |

In this manner, users define a balanced layout definition by editing a simple layout file, with which a complete display protocol can be built on the fly based on the current data selection, user preference, and built-in application linking rules. This allows the users to review and interact with the images in the way that the layout is specified.

Figure 11:
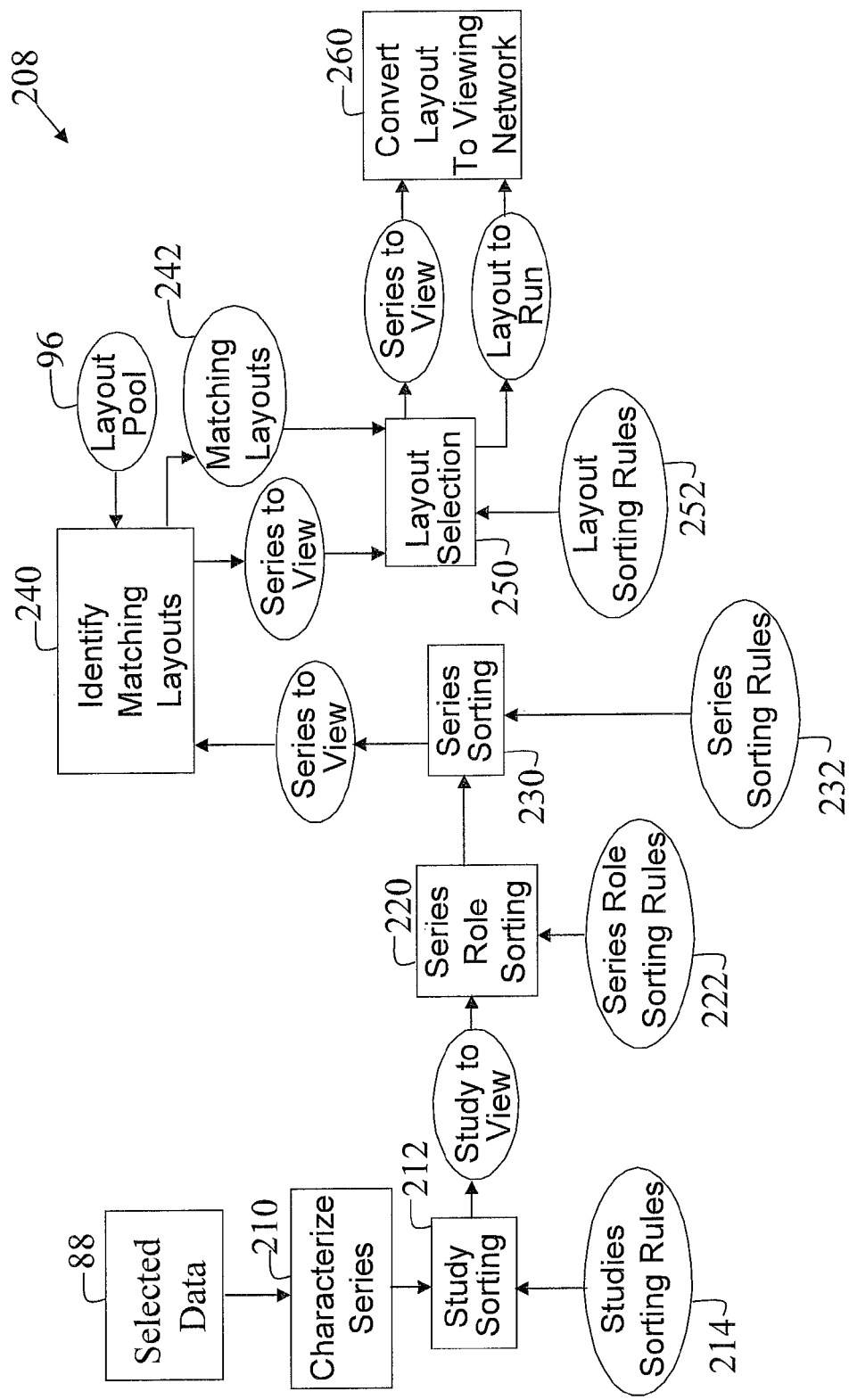
FIG. 11 is a flow chart of a layout selection.

With continuing reference to FIGS. 2 and 10 and further reference to FIG. 11, in step 208, the layout device 94 performs data sorting and layout selection. In step 210, a series characterization is performed. More specifically, some series' properties are retrieved and saved in an object of characteristics class, which is then put into a hash table with the series as its key. Some of other information such as group index, which is not part of series' attribute, is obtained from input groups.

When the selected data 88 includes multi studies, the layout manager 94 performs a study sorting 212 based on studies sorting rules 214 and decides which study should be displayed first. For example, the studies sorting rules include a rule by which a newer study has a higher priority than an older study.

In step 220, a series role sorting is performed based on series role sorting rules 222 to select a series which can serve as a reference. For example, a resolution along the z direction is checked in all selected series to determine which one in its group is the best for reference. If the resolution fails to tell the difference, then the modality is used to differentiate them with the following order CT/MR/PET/SPECT.

In step 230, the series are sorted based on series sorting rules 232 to determine which series will be used first for data matching purpose. For example, the series are sorted into two groups such as anatomical and functional. For example, the series are sorted based on a modality with following order: PET/SPECT/CT/MR/SC.

For example, functional series, e.g. images generated, for example, with the nuclear imaging system, are sorted based on following priorities:
Registered over non-registered
CT Attenuation Corrected (CTAC) over non-attenuation corrected (NonAC)
Larger field of view (FOV) over smaller FOV
Longer Z coverage over shorter Z coverage (such as whole body over brain)
Static over dynamic
Reformatted over non-reformatted
Newer over older For example, anatomical series, e.g. images generated with, for example, the CT scanner, are sorted based on the following priorities:
Higher resolution over lower resolution
Larger FOV over smaller FOV (such as low dose CT over diagnose CT)
Longer Z coverage over shorter Z coverage
Contrast enhanced over non-contrast enhanced
Newer over older After the sorting, series are picked alternately from functional group and anatomical group if possible until limit is reached (3 series for a non-comparison case). For example, if one CT, one CTAC PET, one NonAC PET and one SC series are selected, then in the final list are CTAC PET/CT/NonAC series.

In step 240, all applicable matching layouts 242 among all available layouts are identified for data selection. For example, the layout identification algorithm is:

---
Characterize input series
for each layout
   get all required input characteristics
   for each input characteristics
      get a list of series matching this characteristics
      if there isn't any series in the list which is not included
         the layout is considered not matched
         continue on next layout
      else
         include the new series and
         continue on next required input characteristics
   add this layout into matched layout list
sort all matched layouts

---

The layouts are selected or sorted 250 based on input matching number, user favorite rating, and layout sorting rules 252 to decide which layout should be launched first. For example, a user selects one PET and one CT and there are one layout displaying PET and another displaying PET/CT. The layout sorting rules 252 include a rule by which the PET/CT layout gets higher priority regardless of favorite rating. Favorite rating starts to play a role when there are more than one layout matching the same number of inputs. Another example of the rule is the rule which gives a priority to the current layout if the current layout matches the current series selection.

In this manner, the optimal layout is automatically selected based on the data selection. This is based on built-in study and series sorting algorithms, the list of available layouts and the user favorite rating, and the layout that is currently being displayed.

Figure 12:
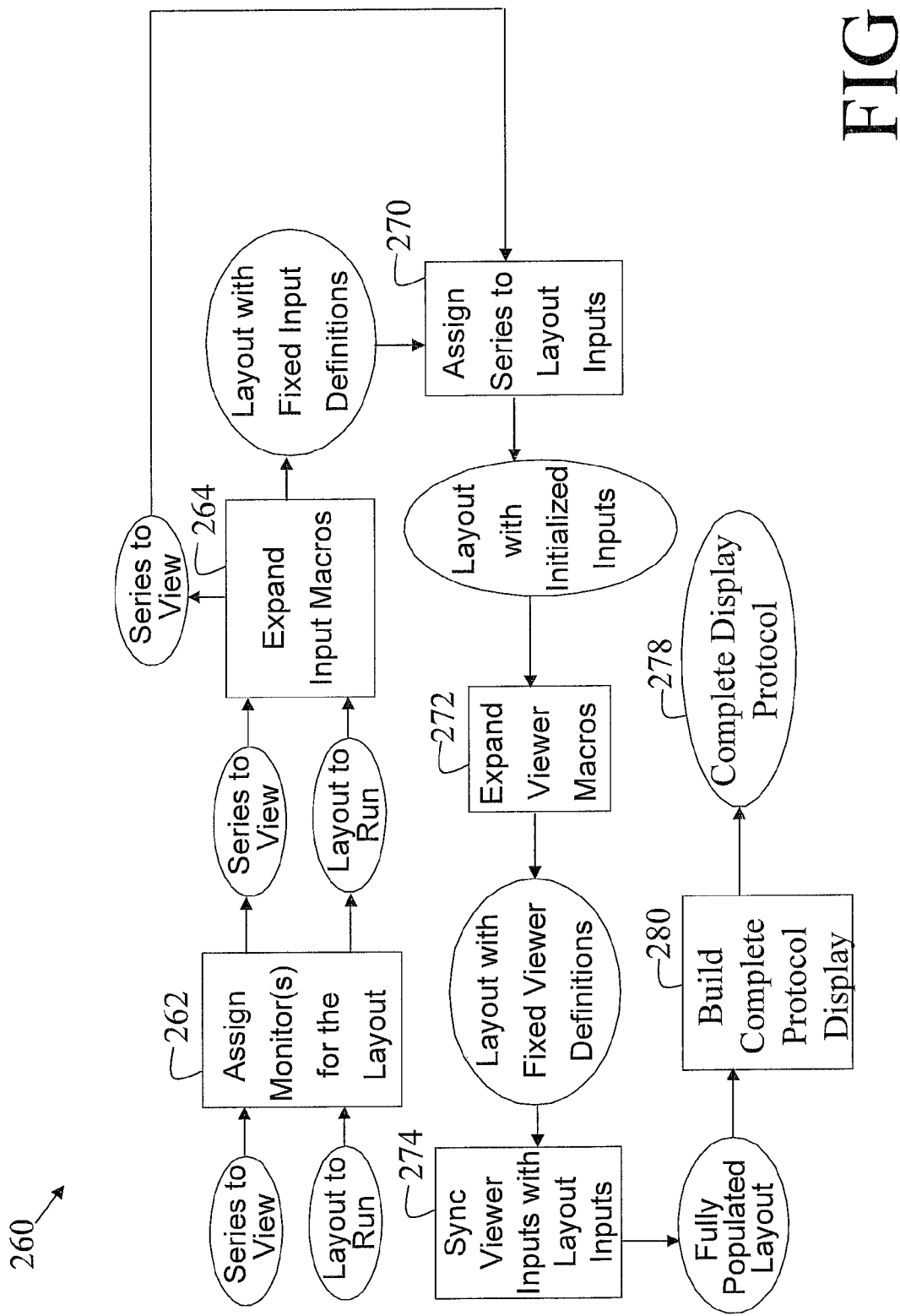
FIG. 12 is a flow chart of converting the selecting layout to a viewing network.
Figure 13:
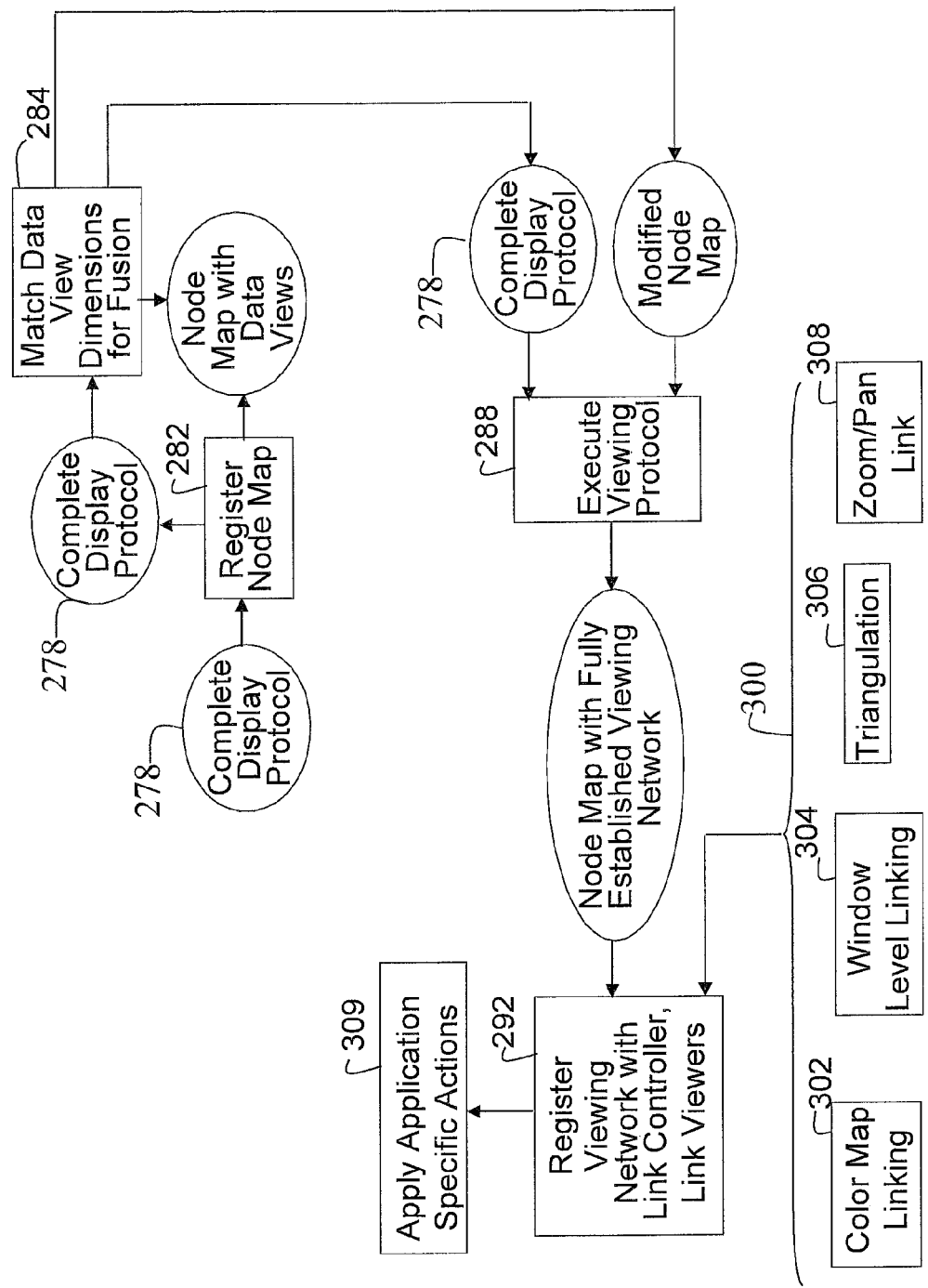
FIG. 13 is a continuation of the flow chart of converting the selected layout to a viewing network.

With continuing reference to FIGS. 2, 10 and 11 and further reference to FIGS. 12 and 13, the layout device 94 converts 260 the selected layout to a viewing network. The layout manager 94 assigns 262 monitors to the selected layout. For example, some layouts require multiple monitors for display. Effective viewing areas of each monitor are computed and use to configure a monitor configure object, which is used by the protocol engine. As a result, the viewers are displayed in monitors where the viewers are supposed to be displayed without crossing a monitor boundary.

In step 264, input macros are expanded. As described above, layout inputs are defined through characteristics objects, which may include some macro key words such as "All" for inputReference field. For example, all series available that meet the defined criterion, are searched. The input is expanded into several concrete inputs. For example, the layout input contains a macro "All" in the inputReference field:

---
<inputs>
  <Characteristics>
    <inputReference>All</inputReference>
    <modality>PET</modality>
  </Characteristics>
</inputs>

---

Assuming there are three series available, among which two series are PET image data and one series is SPECT image data. The input "All" is expanded into two input definitions, including "Input1" for PET modality and "Input2" for SPECT modality:

```
<inputs>
    <Characteristics>
        <inputReference>Input1</inputReference>
        <modality>PET</modality>
    </Characteristics>
    <Characteristics>
        <inputReference>Input2</inputReference>
        <modality>SPECT</modality>
    </Characteristics>
</inputs>
```

After macro expansion, each series are assigned 270 to the layout input which characteristics matches the series.

In step 272, viewer macros are expanded. Generally, every viewer can have a maximum of two inputs. Each input can potentially have macros such as "All" for inputReference. A viewer's input characteristics defines a query. If there is more than one series that meet the criterion for one viewer input, the extra viewer(s) are spawned. For example, the extra viewers are tabbed together in the same area. The scope of the search is limited within all series the layout has been assigned to.

In step 274, viewer inputs are synched with layout inputs. This step makes sure that the viewer's input is assigned with the series.

Once a layout definition is fully populated, a complete display protocol 278 is built 280 from the layout definition. The full display protocol describes what components are needed and how the components need to be connected.

In step 282, a node map is registered. Since data views (packed image data for viewers to display) are provided by application data model, this step helps to label them with proper names so that they can be connected properly.

In step 284, data view dimensions are matched for a possible fusion application. For example, when one viewer gets assigned two data views with different number of dimensions, this step will expand the data view with fewer dimensions to match the one with more dimensions. For example, a viewer has a CT data as its underlay, which is one-dimensional, e.g. it contains only one volume, and has a PET data as its overlay, which is two-dimensional, e.g. meaning it contains multiple volumes at the same location but from different times. The CT data is expanded to have the same number of volumes as the PET data by "duplicating" itself. No actual pixel data is duplicated but only the reference points are added. E.g., the user is allowed to navigate through all dimensions of a multiple dimensional image data and to fuse it with other modality data with or without the same dimensions.

In step 288, a viewing protocol is executed. A protocol engine 290 uses the complete display protocol 278 to instantiate all software objects and connect them to establish the viewing network.

In step 292, a viewing network is registered with a link controller 294 which automatically links viewers. Although the protocol engine 290 establishes an initial viewing network, in a fusion display, for example, color map links need to be changed based on each viewer's fusion state. The link controller 294 acts as a manager and administers the entire linking behavior, e.g. adding/removing links. More specifically, the link controller 294 automatically links viewers to the associated image data based on a set of rules 300 including rules for a color map linking 302, a window level linking 304, triangulation 306 and a zoom/pan presentation linking 308 as described below.

Examples of rules for a color map linking 302:

| If same group (in case of comparison)<br>If common modality<br>If non-fused viewer, or same pin if fused viewer<br>Same color stripe (lookup table) |
|---|

Example of rules for a window level linking 304:

| If same group (in case of comparison)<br>If common series<br>Same upper/lower, window/center |
|---|

Example of rules for triangulation 306:

| If same group (in case of comparison)<br>Triangulation of all TSC views |
|---|

Examples of rules for zoom/pan linking 308:

| If same group (in case of comparison)<br>If common orientation (transverse, sagittal or coronal)<br>Same zoom and pan |
|---|

In this manner, the viewers are automatically linked to the image data associated with the viewers based on a set of built-in linking rules for all layouts. The rules are automatically enforced even when some viewers are destroyed or series is replaced until the user specifically makes a change.

In step 309, the layout manager 94 applies application specific actions in an orderly manner.

With continuing reference to FIGS. 2 and 10, for easy switching of layouts, the layout manager 94 preserves 310 the viewing context, including preservation of a color map 312, window level 314, hot spot 316, zoom/pan factors 318, image index offset 320, start position 322 and free dimension 324. Each viewing context is stored under a certain key, which is generated based on certain set of rules (in some cases, these are also the rules used to generate across viewer links). After layout is switched, the keys for every viewer and data views attached to it are re-generated. Using the keys, the viewing context is fetched from a common hash table. If such viewing context exists for a given key, it should be reapplied to the viewer and data view from which the key is generated. Of course, it is contemplated that the other features can be preserved such as region of interest (ROI), labels, tags, markers, and the like.

To preserve the color map 312, a color map of each data view is retrieved and saved in a hash table under a unique key string which uses namespace naming convention. The color map will be transferred to next layout's data view as long as both layouts share the same group index, the same modality and the same pin (for fused case).

For example, for a fused case, a unique key string is:

Identifier.Modality.Pin.GroupIndex, where Identifier is "Colormap";
Modality is one of the following key words "PET", "CT", "MR" or "SPECT";
Pin means "underlay" or "overlay" depending on where the data view is attached; and GroupIndex indicates which group the color map is pulled from in case of group comparison (for non-comparison layout, the value is 0).

As another example, for a non-fused case, a unique key string is:

Identifier.Modality.GroupIndex, where Identifier is "Colormap";
Modality is one of the following key words "PET", "CT", "MR" or "SPECT"; and
GroupIndex indicates which group the color map is pulled from in case of group comparison (for non-comparison layout, the value is 0).

The window level is preserved 314 by using a following exemplary key string:

Identifier.SeriesHashCode.RotationMIP.GroupIndex, where Identifier is "WindowLevel";
SeriesHashCode is the hash code of the series; and
RotationMIP is a Boolean indicating if the window level is pulled from a MIP viewer (window level is not linked to/from an MIP viewer.)

Since there is only one hot spot per group, the hot spot is preserved 316 by using an exemplary key string:

Identifier.GroupIndex, where Identifier is "Geo".

Zoom and Pan factors are kept in displayed area window. Only displayed area window needs to be preserved. Zoom and Pan Factors are preserved 318 by using an exemplary key string:

Identifier.SeriesHashCode.Orientation.ViewerType.GroupIndex, where Identifier is "ZoomPan";
SeriesHashCode is the hash code of the series;
Orientation is image orientation specified in viewer configuration; and
ViewerType is viewer type that is also specified in viewer configuration object.

The image index offset, which is an attribute of viewer's control model, is preserved 320 by using an exemplary key string for a non fused case:

Identifier. SeriesHashCode.Orientation.ViewerType.GroupIndex, where Identifier is "IndexOffset";
SeriesHashCode is the hash code of the series;
Orientation is image orientation specified in viewer configuration; and
ViewerType is viewer type that is also specified in viewer configuration object.

For a fused case, the image index offset is preserved 320 by using another exemplary key string:

Identifier.UnderlaySeriesHashCode.OverlaySeriesHashCode.Orientation.ViewerType.GroupIndex, where Identifier is "IndexOffset";
SeriesHashCode is the hash code of the series;
Orientation is image orientation specified in viewer configuration; and
ViewerType is viewer type that is also specified in viewer configuration object.

The start position is preserved 322 by using the same key as used to preserve the image index offset. The start position is an attribute of indexer control model which itself is a part of viewer's control model.

In this manner, viewing context is automatically and intelligently preserved when switching layouts. Viewing Context includes color maps for modalities of series being reviewed, window levels for series being reviewed, zoom/pan factor for different image orientations that are displayed, lesions that are located by the user, image index, and others.

Free dimension is preserved 324 by using the same key as used to preserve the image index offset. The free dimension is an attribute of indexer control model which itself is a part of viewer's control model.

With continuing reference to FIG. 2, a fusion controller 326 controls display of fused images via a toggle switch 328. Generally, images are frequently displayed in a non-fused mode with a demand to occasionally review images in the fused fashion. In one embodiment, all viewers are defined as fused viewers, e.g. in the non-fused mode, the viewer status is changed to a non-fused. The invisible data view is deactivated so that it will not be affected by any changes occurred in the same viewer or other viewers. If the viewer status is changed to a fused mode, the link controller 294 first disconnects the viewer and its image data from its current color map link, and then looks for a suitable color map link which takes care of fused viewers. If such link exists, the link controller includes the new fused viewer along with its data views into the link. If such link does not exist, the link controller creates such a viewer. A similar process happens when a fusion is turned off.

Different set of templates, that define what image information is and how it should be displayed along with image pixel data, is used to handle image information annotation. When the fusion is turned on, a fused annotation template is used. When the fusion is turned off, depending on which data view is visible, a corresponding non-fused annotation template is used. To avoid confusion, an ROI measurement reflects one image at a time. When the fusion status is changed, an ROI association is changed accordingly.

In this manner, the single toggle 328 is provided to turn fusion on/off in any individual viewer within a layout with annotation, region of interest measurements and linking behavior automatically adjusted to the change of the fusion status so that consistent application behavior is maintained.

Figure 14:
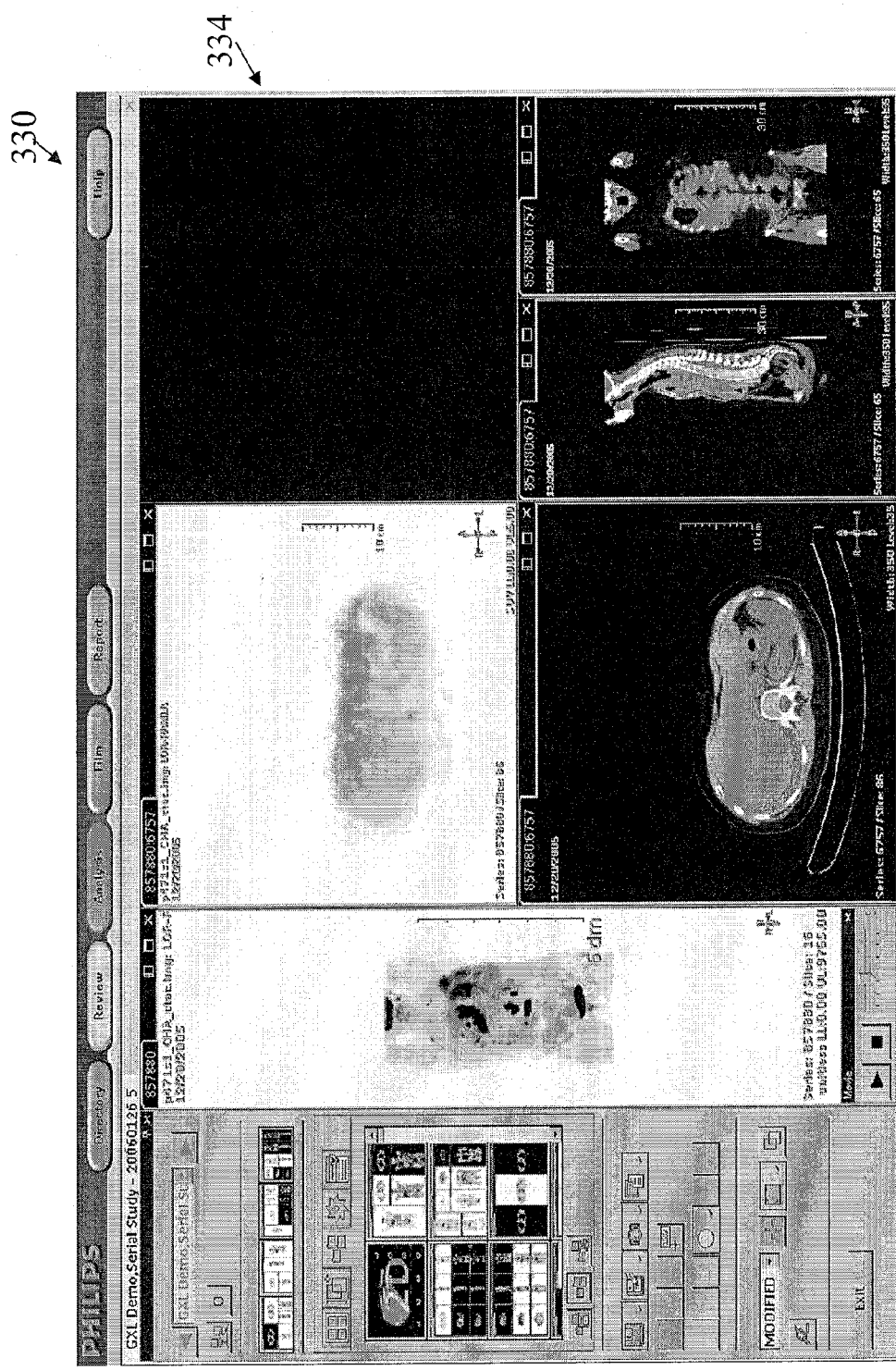
FIG. 14 is an image of one of the layouts.
Figure 15:
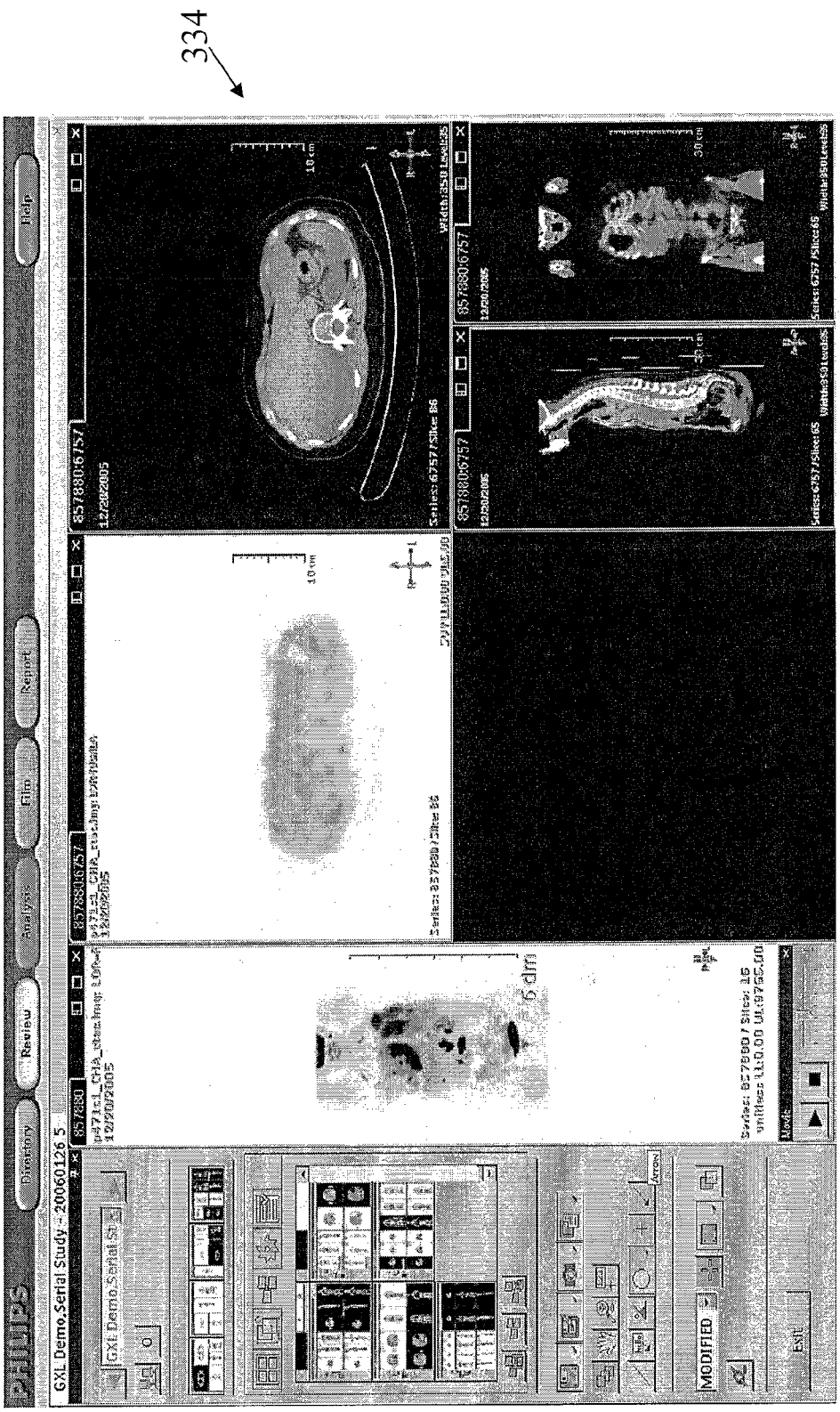
FIG. 15 is an image of a modified layout of FIG. 14.

With reference to FIGS. 14 and 15, the users are allowed to modify existing display and save the modified display as a new layout. For example, the user inspects the current display 330 and moves image 332 into position 334. All viewers that are on screen are searched. Their position, size, fusion state, zoom factors, and monitor information are fetched. Layout inputs are populated when an associated layout is processed.

At runtime, layout inputs are populated and they can also be replaced. A fully initialized layout contains no macros. For example, a layout has two inputs which are defined as:

```
<inputs>
  <Characteristics>
      <inputReference>Input1</inputReference>
      <modality>Anatomical</modality>
  </Characteristics>
  <Characteristics>
      <inputReference>Input2</inputReference>
      <modality>FunctionalAnatomical</modality>
  </Characteristics>
</inputs>
```

After the layout is fully populated, the inputs of its working copy become, for example:

```
<inputs>
    <Characteristics>
        <inputReference>Input1</inputReference>
        <modality>MR</modality>
    </Characteristics>
    <Characteristics>
        <inputReference>Input2</inputReference>
        <modality>CT</modality>
    </Characteristics>
</inputs>
```

The same level of modality specificity that the original layout supports is maintained when the layout is modified and saved. From the example above, when such layout is loaded, only MR & CT can be handled. To overcome this, the following scheme can be used:

```
Go through each input
    If the populated input supports a subset of data range that the original input does
        Then the original input will be used as the new layout input definition
    Otherwise
        Promote the populated input to the same modality specificity as the original
```

Figure 16:
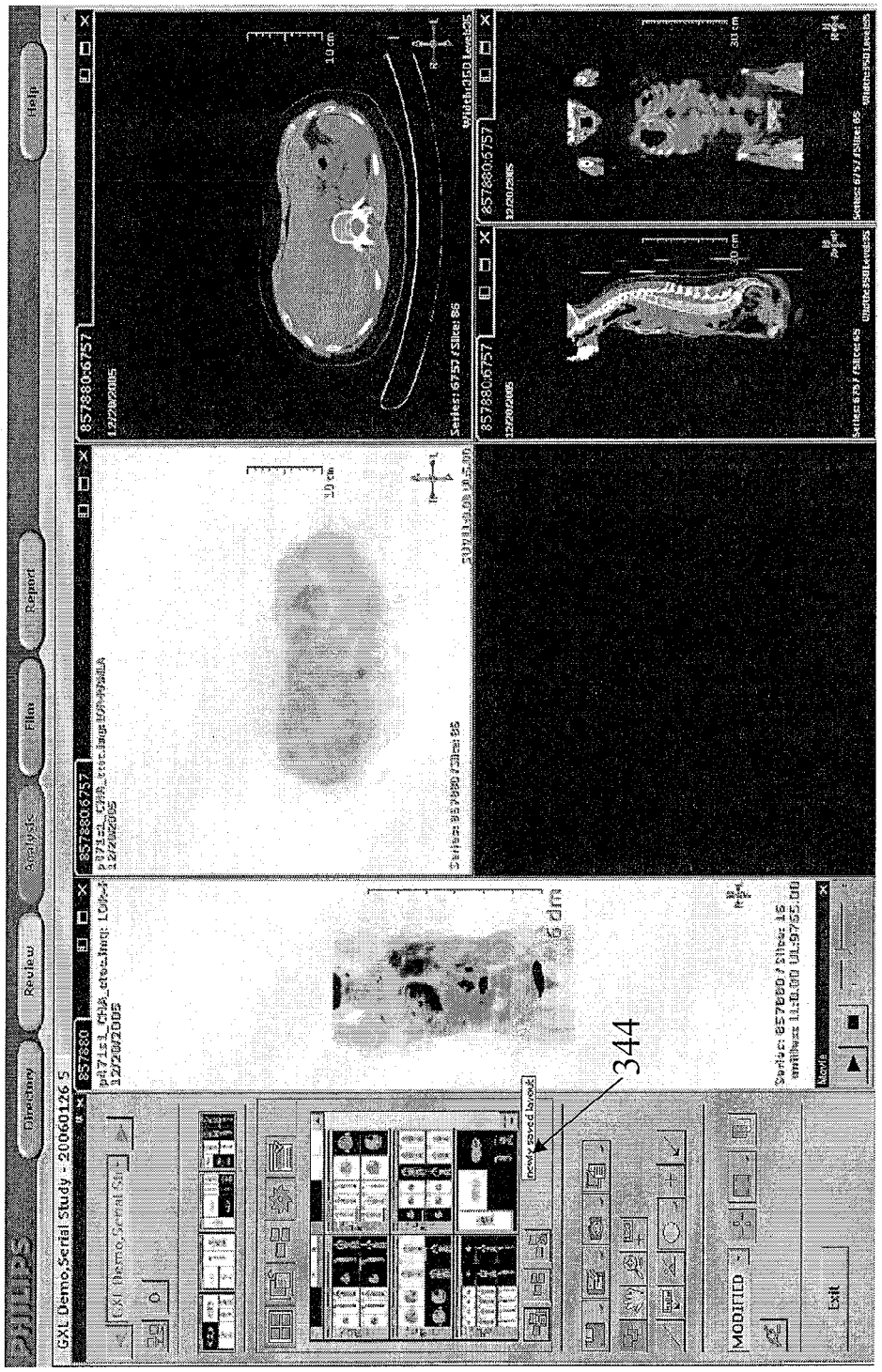
FIG. 16 is an image showing the layout of FIG. 15 and a newly saved icon for this layout.

With reference to FIG. 16, a layout icon 344 is created on the fly. A screen capture of an entire image display area is performed. A thumbnail out of the capture is made and saved as a part of the new layout's icon.

Figure 17:
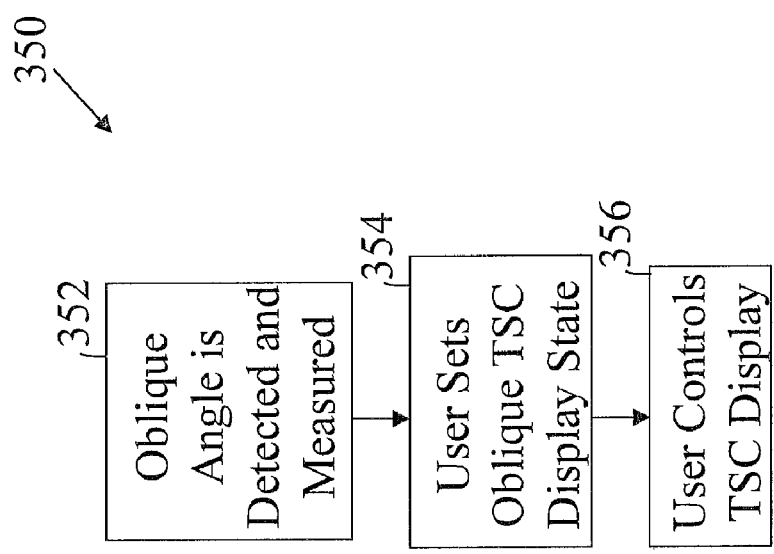
FIG. 17 is a flow chart of control of oblique TSC display.

With reference to FIG. 17, the users handle the display 350 of the oblique images. In step 352, an oblique angle is detected and measured. When a volume is reformatted, two pieces of oblique information are stored in DICOM file: (1) row/column vectors, and (2) view code sequence, from which the original oblique transformation can be uniquely constructed. Once the original oblique transformation is constructed, the original oblique rotation angles or the rotation of each axis from its original direction can be determined In step 354, user sets an oblique TSC display state based on the oblique angle. When a volume is loaded, the user requests permission from the application to view the images at the oblique TSC instead of the normal TSC. The permission to use the oblique display is based on rules. The rules, for example, are based on the oblique angle measurement, the existence of the oblique angle in one of the images, and the layout configuration. For example, the permission is granted if the oblique angle is from about 0° to about 42.5°. If the volume is not tilted, the permission is denied. In step 356, the user controls TSC display based on different oblique angles. The user can set any series as reference, so the actual oblique angle is derived from the reference image. For example, a first series has a 10° rotation along axial axis and a second series has a 20° rotation along axial axis. The user can display or fuse the first and second series by aligning the first or second series with either series. The series can be displayed in non-oblique and/or oblique fashion.

In this manner, users can edit a currently displayed layout by re-positioning viewers (components that display images on screen), resizing viewers, changing fusion status of viewers, adjust zoom/pan factor of viewers, destroying viewers, changing viewing series, etc, and caching it in memory and saving it. This makes creating a viewing network with desired initializations, which used to be the task of software developers, as easy as saving a modified word processing document.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A medical imaging system comprising:
one or more displays;
a viewer device for generating an interactive user interface screen on the display, which viewer device enables a user to simultaneously inspect selected image data of multiple patients or multiple images;
a registration device which identifies a global reference image in the selected image data, and determines a registration matrix which aligns an image with the global reference image; and
a group registration device which registers or aligns images of the selected groups and is programmed to perform steps of:
selecting a reference image in a first group;
selecting a reference image in a second group;
computing registration between the images of the first and second groups as $$M_{r1r2} = M_{r1}^{-1} M_{r2},$$

where $M_{r1r2}$ is the registration between the images of the first and second groups,
$M_{r1}$ is a registration of the selected first group reference image with respect to the global reference image, and
$M_{r2}$ is the registration of the selected second group reference image with respect to the global reference image.

2. The system as set forth in claim 1, wherein the viewer device includes:
a patient viewer manager which launches each patient for viewing in a preselected order; and
a patient viewing component which displays image data of each patient.

3. The system as set forth in claim 1, wherein a patient viewing component displays image data of multiple patients for direct side by side comparison on one of a single display or the displays.

4. The system as set forth in claim 1, further including:
a layout device which automatically selects a layout for display of the images based at least on the selected image data and user preferences.

5. The system as set forth in claim 1, further including:
a comparator which compares selected viewing groups of images.

6. The system as set forth in claim 1, wherein the group registration device is programmed to perform steps of:
identifying at least a first point in a first group image;
determining coordinates of the first point;
identifying at least a second point in a second group image;
determining coordinates of the second point; and
computing a registration relation between the first and second points.

7. The system as set forth in claim 1, wherein the images are generated by scanners which include at least one of: PET, SPECT, MRI, ultrasound, fluoroscopy, CT, and digital x-ray.

8. A method of medical imaging comprising:
generating an interactive user interface screen on a display;
simultaneously inspecting selected image data of multiple patients or multiple images on the display;
identifying a global reference image in the selected image data;
determining a registration matrix which aligns a registering image with the global reference image;
comparing a frame of reference of remaining images to a frame of reference of the global reference image; and
propagating the registration matrix to the images whose frames of reference coincide with the frame of reference of the registering image.

9. A non-transitory computer readable memory carrying software which is run on one or more processors to perform the method as set forth in claim 8.

10. A medical imaging system including:
at least one display;
one or more processors programmed to perform the method as set forth in claim 8.

11. A medical imaging method comprising:
generating an interactive user interface screen on a display;
simultaneously inspecting selected image data of multiple patients or multiple images on the display;
identifying a global reference image;
defining a relationship between each image and the global reference image via a registration matrix, the registration matrix being an identity matrix;
determining a registration relation between first and second images from a registration relationship between the first image and the global reference image, and a registration relationship between the second image and the global reference image; and
aligning the first and second images to the selected global reference image.

12. The method as set forth in claim 11, further including:
comparing a frame of reference of each image to the frame of reference of the global reference image; and
based on the comparison, propagating the registration matrix to the images whose frames of reference coincide with the frame of reference of the image.

13. The method as set forth in claim 11, wherein determining the registration relation between the first and second images is calculated as $$M_{r1r2} = M_{r1}^{-1} M_{r2},$$

where $M_{r1r2}$ is the registration relation between the first and second images,
$M_{r1}$ is the registration of the first image with respect to the global reference image; and
$M_{r2}$ is the registration of the second image with respect to the global reference image.

14. A non-transitory computer readable memory carrying software which is run on one or more processors to perform the method as set forth in claim 11.

15. A medical imaging system including:
at least one display;
one or more processors programmed to perform the method as set forth in claim 11.

16. A medical imaging method comprising:
generating an interactive user interface screen on a display;
simultaneously inspecting selected image data of multiple patients or multiple images on the display;
identifying a global reference image;
aligning all images to the selected global reference image;
comparing a frame of reference of each image to the frame of reference of the global reference image
determining a 3D position of a point of interest in one image; based on the determined position of the point of interest in the image, determining positions of corresponding points of interest in associated images;
retrieving a position of the point of interest in the display coordinate system;
transforming the display coordinates of the point of interest into patient coordinates in accordance with image position and orientation;
determining a position of an original point of interest in the patient coordinate system;
transforming coordinates of the original point into the common coordinate system; and
updating the associated images.

17. A medical imaging method comprising:
generating an interactive user interface screen on a display;
simultaneously inspecting selected image data of multiple patients or multiple images on the display;
comparing selected viewing groups of images, the images in each group having a known registration relation to a common global reference;
selecting a reference image in a first group;
selecting a reference image in a second group;
computing registration between the images of the first and second groups from the registration of the selected first group reference image with respect to the global reference image and the selected second group reference image with respect to the common global reference image; and
computing registration between the images of the first and second groups as $$M_{r1r2} = M_{r1}^{-1} M_{r2},$$

where $M_{r1r2}$ the registration between the images of the first and second groups,
$M_{r1}$ is a registration of the selected first group reference image with respect to the global reference image, and
$M_{r2}$ is the registration of the selected second group reference image with respect to the global reference image.

* * * * *